United States Patent

Cook et al.

[11] Patent Number: 5,151,436
[45] Date of Patent: Sep. 29, 1992

[54] DERIVATIVES OF THIOFORMAMIDE

[75] Inventors: David C. Cook, London; Terance W. Hart, Brentwood; Iain M. Mc Lay, Loughton; Malcolm N. Palfreyman, Upminster; Brian W. Sharp, Hornchurch; Roger J. A. Walsh, Rayleigh, all of England

[73] Assignee: Rhone-Poulenc Sante, Antony, France

[21] Appl. No.: 571,101

[22] Filed: Aug. 23, 1990

Related U.S. Application Data

[63] Continuation-in-part of Ser. No. 285,219, Dec. 16, 1988.

[30] Foreign Application Priority Data

Dec. 18, 1987 [GB] United Kingdom ............... 8729521
Jun. 16, 1989 [GB] United Kingdom ............... 8913865

[51] Int. Cl.5 ............... A61K 31/435; A61K 31/47; A61K 31/445; C07D 215/06; C07D 211/72; C07D 211/84

[52] U.S. Cl. ............... 514/314; 514/212; 514/277; 514/311; 514/318; 514/332; 514/346; 514/357; 514/880; 514/375; 540/597; 546/164; 546/175; 546/194; 546/265; 546/266; 546/267; 546/281; 546/261; 546/263; 546/264; 546/291; 546/293; 546/300; 546/301; 546/302; 546/331; 546/340

[58] Field of Search ............... 546/291, 293, 300, 301, 546/302, 331, 340, 261, 263, 264, 265, 266, 267, 164, 175, 194, 281; 514/277, 346, 357, 880, 332, 375, 212, 311, 314, 318; 540/597

[56] References Cited

U.S. PATENT DOCUMENTS 5,037,835 8/1991 Efflard et al. ............... 546/165

*Primary Examiner*—Johann Richter
*Attorney, Agent, or Firm*—Morgan & Finnegan

[57] ABSTRACT

Therapeutically useful thioformamide derivatives of the formula:

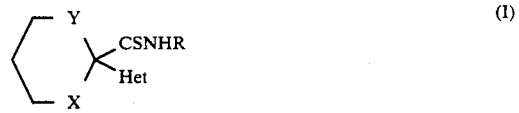

(I)

wherein R represents alkyl, Het represents pyrid-3-yl, isoquinolin-4-yl, tetrahydroquinolin-3-yl, quinolin-3-yl, pyridazin-4-yl, pyrimid-5-yl, thiazol-5-yl, thieno[2,3-b]-pyridin-5-yl, pyrazin-2-yl, indol-3-yl and thieno[3,2-b]-pyridin-6-yl, Y represents ethylene, methylene or a valency bond, and X represents carbonyl, hydroxymethylene, $>C=NOR^1$, $>C=NN(R^1)_2$ or $>C=NN(R^1)CON(R^1)_2$ in which $R^1$ represents hydrogen or optionally substituted alkyl, benzyl, phenethyl, 1-naphthylmethyl, 2-naphthylmethyl or pyrid-3-ylmethyl, or two $R^1$ substituents on the same nitrogen atom may together form an optionally substituted alkylene radical chain and salts thereof, processes for their preparation and compositions containing them are described.

8 Claims, No Drawings

DERIVATIVES OF THIOFORMAMIDE

This application is a continuation-in-part of application Ser. No. 285219 filed Dec. 16, 1988, which is hereby incorporated by reference.

This invention relates to new therapeutically useful thioformamide derivatives, to processes for their preparation and to pharmaceutical compositions containing them.

The new thioformamide derivatives of the present invention are those compounds of the general formula (I) hereinafter depicted, wherein R represents a straight- or branched-chain alkyl radical containing from 1 to 4 carbon atoms, Het represents an aromatic heterocyclic radical containing one or two nitrogen atoms (optionally substituted by a straight- or branched-chain alkyl or alkoxy radical containing 1 to 4 carbon atoms or by a halogen atom), selected from pyrid-3-yl, isoquinolin-4 TM yl, tetrahydroquinolin-3-yl, quinolin-3-yl, pyridazin-4-yl, pyrimid-5-yl, thiazol-5-yl, thieno[2,3-b]pyridin-5-yl, pyrazin-2-yl, indol-3-yl and thieno[3,2 TM b]pyridin-6-yl, Y represents an ethylene or preferably methylene radical, or preferably a valency bond, and X represents a carbonyl or hydroxymethylene group or a group of the formula: $>C=NOR^1$, $>C=NN(R^1)_2$ or $>C=NN(R^1)CON(R^1)_2$ in which the symbols $R^1$, which may be the same or different, each represents the hydrogen atom cr preferably a straight- or branched-chaln alkyl radical containing from 1 to 4 carbon atoms which is unsubstituted or substituted by one or more substituents selected from $C_{2-4}$-alkenyl, carboxy, $C_{2-5}$-alkoxycarbonyl, hydroxy, $C_{1-4}$-alkoxy, carbamoyl (unsubstituted or substituted by one or two $C_{1-4}$-alkyl groups), amino, C amino and di-$C_{1-4}$-alkylamino groups (e.g. $R^1$ may represent a t.butyl or 2,3-dihydroxypropyl radical), or preferably represents a benzyl, phenethyl, 1-naphthylmethyl, 2-naphthylmethyl or pyrid-3-ylmethyl radical each of which may be substituted on the ring by one or more halogen atoms or hydroxy, $C_{1-4}$-alkyl, $C_{1-4}$-alkoxy (alkoxy being unsubstituted or substituted as defined for alkyl groups represented by $R^1$), cyano, nitro, trifluoromethyl, carboxy, $C_{1-4}$-alkylamino, $C_{2-5}$-alkanoylamino or $C_{2-5}$-alkoxycarbonyl groups or two $R^1$ substituents on the same nitrogen atom may together form a straight or branched chain alkylene radical containing from 4 to 6 carbon atoms in the chain which is unsubstituted or substituted as defined for alkyl radicals represented by $R^1$ (e.g. 1-methoxymethyltetramethylene) and pharmaceutically acceptable salts thereof.

Preferably X represents the carbonyl group or a group of formula $>C=NOR^1$ as hereinbefore defined.

Preferably Het represents 3-pyridyl, 6-chloropyrid-3-yl, 5-bromopyrid-3-yl, 3-quinolinyl, 4-isoquinolinyl or 5-pyrimidyl.

The presence of a hydroxy group on the ring creates an asymmetry in the molecule which, in association with the adjacent asymmetric carbon atom, leads to 4 stereoisomers which, optionally, can be separated into 2 racemic pairs. The racemic pair and its enantiomers of the general formula (II) in which R, Het and Y are as hereinbefore defined, i.e. the compounds in which the hydroxy group is in the trans position relative to the group —CSNHR are preferred.

Furthermore, in certain cases the substituents R and $R^1$ contribute to stereoisomerism. All such forms are embraced by the present invention.

Particular compounds of the present invention are as follows:

A) (±)-N-methyl-2-oxo-1-(3-pyridyl)cyclohexanecarbothioamide
B) (±)-N-methyl-2-oxo-1-(3-quinolinyl)-cyclohexanecarbothioamide
C) (±)-N-methyl-2-oxo-1-(3-pyridyl)cycloheptanecarbothioamide
D) (±)-trans-N-methyl-2-hydroxy-1-(3-pyridyl)cyclohexanecarbothioamide
E) (±)-cis-N-methyl-2-hydroxy-1-(3-pyridyl)cyclohexanecarbothioamide
F) (±)-anti-N-methyl-2-hydroximino-1-(3-pyridyl)cyclohexanecarbothioamide
G) (±)-anti-N-methyl-2-methoxyimino-1-(3-pyridyl)-cyclohexanecarbothioamide
H) (±)-anti-N-methyl-2-benzyloxyimino-1-(3-pyridyl)-cyclohexanecarbothioamide
I) (±)-anti-N-methyl-2-hydroxyimino-1-(3-quinolinyl)-cyclohexanecarbothioamide
J) (2S)-anti-2-(methoxymethyl)-1-[2'-(3-quinolinyl)-2'-methylthiocarbamoylcyclohexylideneamino]-pyrrolidine
K) )2S)-anti-2-(methoxymethyl)-1-[2'-(3-pyridyl)-2'-methylthiocarbamoylcyclohexylideneamino]-pyrrolidine,
L) (±)-anti-N-methyl-2-(2-dimethylaminoethoxyimino)-1-(3-pyridyl)cyclohexanecarbothioamide,
M) (±)-anti-N-methyl-2-(2-aminoethoxyimino)-1-(3-pyridyl)cyclohexanecarbothioamide
N) (±)-anti-N-methyl-2-methoxycarbonylmethoxyimino-1-(3-pyridyl)cyclohexanecarbothioamide
O) (±)-anti-N-methyl-2-carbamoylmethoxyimino-1-(3-pyridyl)cyclohexanecarbothioamide,
P) (±)-anti-N-methyl-2-(2,3-dihydroxypropoxyimino)-1-(3-pyridyl)cyclohexanecarbothioamide
Q) (±)-anti-N-methyl-2-(2-hydroxyethoxyimino)-1-(3-pyridyl)cyclohexanecarbothioamide
R) (±)-N-methyl-2-oxo-1-(6-chloropyrid-3-yl)cyclohexanecarbothioamide
S) (±)-N-methyl-2-oxo-1-(5-bromopyrid-3-yl)cyclohexanecarbothioamide
T) (±)-N-ethyl-2-oxo-1-(3-pyridyl)cyclohexanecarbothioamide
U) (±)-N-ethyl-2-oxo-1-(3-quinolinyl)cyclohexanecarbothioamide
V) (±)-anti-N-methyl-2-dimethylhydrazono-1-(3-quinolinyl)cyclohexanecarbothioamide
W) (±)-anti-N-methyl-2-diethylhydrazono-1-(3-quinolinyl)cyclohexanecarbothioamide
X) (±)-anti-N-methyl-2-benzyloxyimino-1-(3-quinolinyl)cyclohexanecarbothioamide
Y) (±)-anti-N-methyl-2-methoxyimino-1-(3-quinolinyl)cyclohexanecarbothioamide
Z) (±)-anti-N-methyl-2-ethoxyimino-1-(3-quinolinyl)-cyclohexanecarbothioamide
AA) (±)-anti-N-methyl-2-butoxyimino-1-(3-quinolinyl)cyclohexanecarbothioamide
AB) (±)-anti-N-methyl-2-(3-isopropylamino-2-hydroxypropoxyimino)-1-(3-quinolinyl)cyclohexanecarbothioamide
AC) (±)-anti-N-methyl-2-t.butoxyimino-1-(3-quinolinyl)cyclohexanecarbothioamide
AD) (±)-anti-N-methyl-2-prop-2-enoxyimino-1-(3-quinolinyl)cyclohexanecarbothioamide
AE) (±)-anti-N-methyl-2-naphth-2-ylmethoxyimino-1-(3-quinolinyl)cyclohexanecarbothioamide AF) (±)-anti-N-methyl-2-phenethyloxyimino-1-(3-quinolinyl)cyclohexanecarbothioamide AG) (±)-anti-N-methyl-2-naphth-1-ylmethoxyimino-1-(3-quinolinyl)cyclohexanecarbothioamide AH) (±)-anti-N-methyl-2-(3-t.butylamino-2-hydroxypropoxyimino-1-(3-quinolinyl)cyclohexanecarbothioamide AI) (±)-anti-N-methyl-2-isopropoxyimino-1-(3-quinolinyl)-cyclohexanecarbothioamide AJ) (±)-anti-N-methyl-2-(4-hydroxybenzyloxyimino-1-(3-quinolinyl)cyclohexanecarbothioamide AK) (±)-anti-N-methyl-2-(4-fluorobenzyloxyimino)-1-(3-quinolinyl)cyclohexanecarbothioamide AL) (±)-anti-N-methyl-2-(4-fluorobenzyloxyimino)-1-(3-quinolinyl)cyclohexanecarbothioamide AM) (±)-anti-N-methyl-2-(2,3,4,5,6-pentafluorobenzyloxyimino)-1-(3-pyridyl)cyclohexanecarbothioamide AN) (±)-anti-N-methyl-2-isopropoxyimino-1-(3-pyridyl)cyclohexanecarbothioamide AO) (±)-anti-N-methyl-2-t.butoxyimino-1-(3-pyridyl)-cyclohexanecarbothioamide AP) (±)-anti-N-methyl-2-[4-(3-t.butylamino-2-hydroxypropoxy)benzyloxyimino]-1-(3-pyridyl)cyclohexanecarbothioamide AQ) (±)-anti-N-methyl-2-(4-hydroxybenzyloxyimino)-1-(3-pyridyl)cyclohexanecarbothioamide AR) (±)-anti-N-methyl-2-(3-fluorobenzyloxyimino)-1-(3-pyridyl)cyclohexanecarbothioamide AS) (±)-anti-N-methyl-2-(2-fluorobenzyloxyimino)-1-(3-pyridyl)cyclohexanecarbothioamide AT) (±)-anti-N-methyl-2-(3-pyridylmethoxyimino)-1-(3-pyridyl)cyclohexanecarbothioamide AU) (±)-anti-N-methyl-2-(4-nitrobenzyloxyimino)-1-(3-pyridyl)cyclohexanecarbothioamide, AV) (±)-anti-N-methyl-2-(4-cyanobenzyloxyimino)-1-(3-pyridyl)cyclohexanecarbothioamide AW) (±)-anti-N-methyl-2-(3,4-difluorobenzyloxyimino)-1-(3-pyridyl)cyclohexanecarbothioamide AX) (±)-anti-N-methyl-2 TM (4-methoxybenzyloxyimino)-1-(3-pyridyl)cyclohexanecarbothioamide AY) (±)-anti-N-methyl-2-(2-trifluoromethylbenzyloxyimino)-1-(3-pyridyl)cyclohexanecarbothioamide AZ) (±) TM N-methyl-2 TM oxo-1-(4-isoquinolinyl)cyclohexanecarbothioamide BA) (±)-anti-N-methyl-2-benzyloxyimino-1-(4-isoquinolinyl)-cyclohexanecarbothioamide BB) (±)-N-methyl-2-oxo-1-(5-pyrimidyl)cyclohexanecarbothioamide BC) (±)-N-methyl-2-oxo-1-(3-pyridyl)cyclopentanecarbothioamide BD) (±)-anti-N-methyl-2-(4-fluorobenzyloxyimino)-1-(3-pyridyl)cyclopentanecarbothioamide BE) (±)-anti-N-methyl-2-methoxyimino-1-(3-pyridyl)-cyclopentanecarbothioamide BF) (±)-anti-N-methyl-2-benzyloxyimino-1-(3-pyridyl)cyclopentanecarbothioamide.

BG) (±)-anti-N-methyl-2-(2,3,4,5,6-pentafluorobenzyloxyimino-1-(3-pyridyl)cyclohexanecarbothioamide BH) (1S)-anti-N-methyl-2-(3,4-diiluorobenzyloxyimino-1-(3-pyridyl)cyclohexanecarbothioamide as well as their enantiomeric and diastereoisomeric and syn forms, where they exist.

The letters A to BH are allocated to the compounds for easy reference later in the specification, e.g. in. the Table and in the Examples.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastro- intestinal tract, urinary bladder and uterus, including peptic ulcers, irritable bowel syndrome and diverticular disease; irritable bladder syndrome; and premature labor.

The compounds also have utility in the inhibition of head hair loss associated with male pattern baldness, by topical application.

For example, compounds of general formula (I) were submitted to:

Vaso-relaxant Activity Tests

The test methods used were adapted from those described by Winslow et al [Eur.J.Pharmacol., 131, 219–228 (1986)] and Karaki [J.Pharmacol. Methods, 18, 1–21 (1987)] for differentiating vaso-relaxant activity.

Test A: Activity against contractions induced by low $K^+$ concentrations in the isolated rat aorta Thoracic aorta was removed from rats and transverse strips, denuded of endothelium, were suspended in a bath containing Krebs solution. The tension was recorded and a contraction induced by addition of 20 mM $K^+$ (potassium ion) to the bathing solution. The test compound was added to the bath as a solution in increasing cumulative concentration. The concentration in the bathing solution of the test compound which reduced the $K^+$-induced contraction by 90% was determined and expressed in $\mu M$ as the effective concentration ($EC_{90}$), given in Table I.

Test B : Activity against contractions induced by high $K^+$ concentrations in isolated rat aorta The test method was as in Test A except that contractions were induced by addition of 60 mM $K^+$ to the bathing solution. The cumulative addition of solutions of the test compound was conducted and the concentration in the bath reducing the $K^+$-inducedcontraction by 90% was greater than 30 $\mu M$ for Compounds A, B and T, and much greater than 30 $\mu M$ for Compounds D, E and G.

TABLE I

| Compound | Activity Test A $EC_{90}\ \mu M$ |
| --- | --- |
| A | 0.8 |
| B | 0.07 |
| D | 7.5 |
| E | 24 |
| G | 0.3 |
| H | 0.01 |
| J | 0.3 |
| R | 0.24 |
| S | 0.4 |
| T | 0.3 |
| BG | 0.001 |
| BH | 0.003 |

In in vivo tests in the anaesthetized guinea pig, performed according to the method of Dixon W.E. and Brodie T.G., J. Physiol 29, pp 97–173 (1903), Compounds BD, BG and BH affected histamine-induced bronchospasm and blood pressure as follows:

|  |  | % maximum bronchospasm | B.P. (mmHg) |
|---|---|---|---|
|  | Control | 80 | 42 |
| Compound BD | 100 μg/ml | 76 | 49 |
|  | 300 μg/ml | 46 | 43 |
|  | 1000 μg/ml | 22 | 40 |
| Compound BD | 200 μg/ml | 28 (control 72) | 40 (control) |
| Compound BH | 200 μg/ml | 17 (control 73) | 32 (control) |

A nebulized aerosol generated from an aqueous solution having a given concentration was administered for 1 minute to the anaesthetized guinea pigs.

Hypotensive Activity

The intravenous dose required to reduce the mean blood pressure in anaesthetized rat was determined and expressed in μg/kg/min as the effective concentration ($EC_{30}$).

The $EC_{30}$ values for compounds BG and BH are:
BG 0.9 μb/kg/min; BH 0.5 μg/kg/min The compounds of general formula (I) can be prepared by the application or adaptation of known methods, for example as hereinafter identified. By the term "known methods" as used in this specification is meant methods heretofore used or described in the literature.

According to a feature of the present invention, the compounds of general formula (I) wherein X represents the carbonyl group or a group of formula $>C=NOR^1$ or $>C=NN(R^1)_2$ wherein $R^1$ is as hereinbefore defined may be prepared by the reaction of a compound of general formula (III) wherein X' represents the carbonyl group or a group of formula $>C=NOR^1$ or $>C=NN(R^1)_2$ as hereinbefore defined and Het and Y are as hereinbefore defined with an isothiocyanate of the general formula:

$$R-N=C=S$$

wherein R represents a straight- or branched-chain alkyl radical containing 1 to 4 carbon atoms.

The reaction is generally carried out in an anhydrous inert organic solvent such as tetrahydrofuran, dimethylformamide or hexamethylphosphoramide, or a mixture of these solvents, at a temperature from −80° C. to +50° C., in the presence of an organic base such as potassium tert.-butoxide or an organo-lithium derivative such as butyllithium, or of sodium hydride.

According to a feature of the present invention, the compounds of general formula (I) wherein X represents the hydroxymethylene group may be prepared by the reduction of a compound of general formula (I) wherein X represents the carbonyl group.

The reduction is generally carried out in an inert organic solvent such as methanol or dimethylsulphoxide, or a mixture of these solvents at a temperature from −20° C. to +50° C., using an alkali metal borohydride, e.g. sodium borohydride.

According to a feature of the present invention, the compouhds of general formula (I) wherein X represents a group of the formula: $>C=NOR^1$, $>C=NN(R^1)_2$ or $>C=NN(R^1)CON(R^1)_2$ as hereinbefore defined may be prepared by the reaction of a compound of general formula (I) wherein X represents the carbonyl group with a compound of the general formula:

$$NH_2OR^1 \quad (VA)$$

$$NH_2N(R^1)_2 \quad (VB)$$

or $$NH_2N(R^1)CON(R^1)_2 \quad (VC)$$

wherein $R^1$ is as hereinbefore defined or with an acid addition salt (preferably the hydrochloride) thereof.

The reaction is generally carried out in the presence of an inorganic base, e.g. sodium carbonate or sodium acetate in an inert organic solvent, e.g. ethanol, or an organic base, e.g. pyridine, which may serve as the solvent, in an inert organic solvent at a temperature from 0° C. to 120° C.

A stereoselective synthesis may be performed for example as hereinafter described in Reference Examples in which a mixture of enantiomers of general formula (III) wherein X' represents the carbonyl group is reacted with a chiral auxiliary agent, e.g. (S)-1-amino-2-methoxymethylpyrrolidine, before being reacted with a compound of general formula (IV) as hereinbefore described followed by the removal of the chiral auxiliary agent.

According to a feature of the invention, the thioformamide derivatives of general formula (I) wherein R represents the methyl radical and X represents the carbonyl group or a group of the formula $>C=NOR^1$ or $>C=NN(R^1)_2$ as hereinbefore defined may be prepared by the process which comprises reacting methylamine with a dithioester of the general formula (VI) wherein the symbols Het, X' and Y are as hereinbefore defined, and R' represents a straight- or branched-chain alkyl radical containing 1 to 4 carbon atoms, or a benzyl or carboxymethyl radical.

In general, the reaction is carried out with an excess of methylamine, without a solvent or in an organic solvent such as an aromatic hydrocarbon, an ether or an alcohol of low molecular weight, or a mixture of these solvents, at a temperature from 20° to 130° C., optionally under pressure.

It is particularly advantageous for the thiol formed during the reaction to be fixed in the form of a heavy metal salt using a thiol acceptor such as mercuric chloride.

The dithioester of general formula (VI) can be obtained by the following methods:

(1) By reaction of a strong base with a compound of the general formula (III) (wherein Het, X' and Y as hereinbefore defined), followed by reacting the resulting product with carbon disulphide and then with a compound of the general formula:

$$R'-Z \quad (VII)$$

wherein R' is as hereinbefore defined, and Z represents a halogen atom, preferably a chlorine, bromine or iodine atom, or a reactive ester radical, preferably a mesyloxy or tosyloxy radical.

The reaction is generally carried out in an ether such as tetrahydrofuran, to which hexamethylphosphoramide has generally been added, at a temperature between −20° and +50° C.

It is particularly advantageous to employ potassium tert.-butoxide as the strong base. Alternatively the organo-lithium derivatives described above may be employed.

It will be understood that it may be desirable to change one or more of the substituents at an appropriate stage during the synthesis of the compounds of the invention, for example, the compounds of general formula (I) wherein $R^1$ contains a phenyl group substituted by a alkoxycarbonyl group may be alternatively prepared from the corresponding compounds of general formula (I) wherein $R^1$ contains a phenyl group substituted by a carboxy group by the application or adaptation of known methods for such conversion.

The thioformamide derivatives of general formula (I) obtained by the aforedescribed processes can be purified by the usual physical methods, in particular crystallization and chromatography, especially to resolve mixtures of enantiomers using a chiral column.

Compounds of general formula (III) may be prepared by the application or adaptation of known methods for example as hereinafter described in Reference Examples.

Compounds of general formula (III) wherein X represents a group of the formula: $>C{=}NOR^1$ or $>C{=}NN(R^1)_2$ as hereinbefore defined may be prepared by the reaction of a compound of general formula (III) wherein X represents the carbonyl group with a compound of the general formula:

 (VA)

or

 (VB)

wherein $R^1$ is as hereinbefore defined or with an acid addition salt thereof in a similar manner to that hereinbefore described for the preparation of the corresponding compounds of general formula (I).

Compounds of general formula (III) wherein X represents the carbonyl group may be prepared from the corresponding 2-methoxy-1-(Het)-cycloalkanol, by known methods.

Alternatively compounds of general formula (III) wherein X represents the carbonyl group and Y represents an ethylene or methylene radical may be prepared from the corresponding 1-[(Het)bromomethyl] cyclohexanol or 1-[(Het)bromomethyl]-cyclopentanol respectively by known methods.

The compounds of general formula (III) wherein Y, Het and X' are as hereinbefore defined with the proviso that Y is not a direct bond when Het represents optionally substituted pyrazin-2-yl and Y does not represent methylene when Het represents optionally substituted indol-3-yl and their processes of preparation form further features of the present invention.

Compounds of general formula (V) may be prepared by known methods.

By the term "pharmaceutically acceptable salts" as used in this specification is meant salts the anions or cations of which are relatively innocuous to the animal organism when used in therapeutic doses so that the beneficial pharmaceutical properties of the parent compounds of general formula (I) capable of forming salts are not vitiated by side-effects ascribable to those anions or cations.

As well as being useful in themselves as active compounds, acid addition salts of the compounds of general formula (I) capable of forming such salts are useful for the purposes of purification of the parent compounds of general formula (I), for example by exploitation of the solubility differences between the salts and the parent compounds, by techniques well known to those skilled in art. The parent compounds of general formula (I) can be regenerated from their acid addition salts by known methods, for example by treatment with an alkali, e.g. aqueous sodium bicarbonate solution or aqueous ammonia solution.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-$\beta$-hydroxynaphthoates, gentisates and di-p-toluoyltartrates.

As well as being useful in themselves as active compounds, salts of the compounds of general formula (I) capable of forming salts with bases are useful for the purposes of purification of the parent compounds of general formula (I), for example by exploitation of the solubility differences between the salts and the parent compounds, by techniques well known to those skilled in the art.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

The following Examples and Reference Examples illustrate the preparation of compounds according to the present invention.

Unless stated otherwise, all the spectra were recorded at 200 MHz in deuterochloroform; the chemical shifts are expressed in ppm relative to the tetramethylsilane signal. The abbreviations used in the following text are as follows:

s = singlet
d = doublet
t = triplet
m = multiplet
c = unresolved bands
dd = doublet of doublets
dt = doublet of triplets
ddd = doublet of doublets of doublets
dddd = doublet of doublets of doublets of doublets
qq = quartet of quartets

EXAMPLE 1

Compound A

A vigorously stirred solution of ($\pm$)-2-(3-pyridyl)-cyclohexanone (5.3 g, 30 mmol) in anhydrous tetrahydrofuran (50 ml) under argon at $-15°$ C. was treated with potassium t.-butoxide (3.36 g, 30 mmol).

After 60 minutes at 0° C., a solution of methyl isothiocyanate (2.4 g, 33 mmol) in anhydrous tetrahydrofuran (10 ml) was added during 5 minutes. After 2.5 hours at 0° C. the solution was warmed to 20° C. and then poured into a saturated aqueous brine solution (250 ml). The mixture was extracted with ethyl acetate (50 ml) and then with chloroform (3$\times$50 ml). The combined organic extracts were dried over sodium sulphate and then concentrated in vacuo (30° C.; 14 mmHg).

The crude product (7.9 g) was recrystallised from methanol to give ($\pm$)-N-methyl-2-oxo-1-(3-pyridyl)cyclohexanecarbothioamide (4.8 g, 19 mmol), m.p. 188°–190° C. N.M.R. (CDCl$_3$) 1.62–2.06 (m, 4H); 2.42–2.60 (m, 2H); 2.60–2.82 (m, 1H); 2.84–3.06 (m, 1H), 3.16–3.2 (d, 3H); 7.24–7.34 (ddd, 1H); 7.6–7.68 (ddd, 1H); 8.43–8.47 (d, 1H); 8.48–8.54 (dd, 1H); 8.90–9.2 (broad singlet, 1H). Calculated for $C_{13}H_{16}N_2OS$; C, 62.9%; H, 6.5%; N, 11.3%; S, 12.9%. Found C, 62.9%; H, 6.6%; N, 11.3%; S, 13.1%.

REFERENCE EXAMPLE 1

A solution of (±)-trans-1-[(3-pyridyl)bromomethyl] cyclopentanol (10.24 g, 40 mmol) in anhydrous tetrahydrofuran (500 ml) at 0° C. was treated, dropwise during 30 minutes, with a solution of silver perchlorate (9.9 g, 48 mmol) in anhydrous tetrahydrofuran (50 ml). After 60 minutes at 0° C. the mixture was poured into a mixture of saturated aqueous brine solution (500 ml) and 10% w/v aqueous sodium bicarbonate solution (500 ml). The resulting mixture was filtered and then extracted with ethyl acetate (2×500 ml). The combined organic extracts were washed with brine and then dried over sodium sulphate. Concentration in vacuo (30° C.; 14 mmHg) afforded a crude oil which was recrystallized from cyclohexane (120 ml) to give (±)-2-(3-pyridyl)cyclohexanone (6.7 g, 38 mmol), m.p. 78°–80° C. N.M.R. (CDCl$_3$) 1.72–2.12 (m, 4H); 2.12–2.40 (m, 2H); 2.40–2.64 (m, 2H); 3.56–3.72 (dd, 1H); 7.22–7.32 (m, 1H); 7.44–7.54 (ddd, 1H); 8.34–8.42 (dd, 1H); 8.46–8.54 (dd, 1H).

REFERENCE EXAMPLE 2

A solution of 3-cyclopentylidenemethylpyridine (62.2 g, 0.39 mol) in acetone (600 ml) and water (100 ml) was treated with a solution of concentrated sulphuric acid (18.9 g, 0.19 mol) in water (100 ml) at 5° C. The ice-cold solution was treated with 1,3-dibromo-5,5-dimethylhydantoin (55 g, 0.19 mol) during 20 minutes. After 3.5 hours at 0° C. the mixture was treated with sodium bicarbonate (33.6 g, 0.4 mol) followed by water (2 l) and then extracted with ethyl acetate (2×500 ml). The organic phase was removed and washed with 10% w/v aqueous sodium bicarbonate solution (500 ml) followed by water (200 ml) and brine (200 ml).

The crude extract was dried over sodium sulphate and then filtered through a column of flash silica gel (10 cm×2.4 cm diameter). After concentration in vacuo (20° C., 14 mmHg) the dark oil crystallized on standing to give (±)-trans-1-[(3-pyridyl)bromomethyl]-cyclopentanol (56 g, 0.22 mol) melting point 92°–94° C. Calculated for $C_{11}H_{14}BrNO$, C, 51.6; H, 5.5; Br, 31.2; N, 5.5%. Found C, 51.9; H, 5.6; Br, 30.6; N, 5.5%.

N.M.R (CDCl$_3$); 1.36–2.06 (c, 8H); 2.32–2.46 (broad singlet, 1H); 5.02 (s, 1H); 7.24–7.34 (ddd, 1H); 8.0–8.1 (ddd, 1H); 8.52–8.56 (dd, 1H); 8.62–8.66 (d, 1H).

REFERENCE EXAMPLE 3

A suspension of cyclopentyltriphenylphosphonium bromide (226 g, 0.55 mol) in anhydrous tetrahydrofuran (1000 ml) at 2° C. was treated with vigorous stirring under an atmosphere of argon, with potassium t-butoxide (61.7 g, 0.55 mol). The dark red mixture was stirred at 5° C. for 80 minutes and then treated with pyridine-3-carbaldehyde (58.9 g, 0.55 mol) during a period of 20 minutes. The reaction mixture was stirred at 0° C. for 2 hours and then at 20° C. for 18 hours. The tetrahydrofuran was removed in vacuo (30° C.; 14 mmHg) and the residue extracted with pentane (2×500 ml). After treatment with decolorizing charcoal (5 g) the mixture was filtered through a plug of flash silica gel (Merck 70–230 mesh (13 cm×2 cm diameter). The filtrate was concentrated in vacuo (30° C., 14 mmHg, then 20° C.; 0.01 mmHg) to afford 3-cyclopentylidenemethylpyridine (54 g, 0.34 mol,) as an oil which was used without further purification. N.M.R. (CDCl$_3$) 1.6–1.95 (m, 4H); 2.4–2.65 (m, 4H); 6.26–6.34 (m, 1H); 7.16–7.25 (ddd, 1H); 7.56–7.65 (ddd, 1H); 8.52–8.52 (d, 1H).

REFERENCE EXAMPLE 4

A 4 1 mixture of (±)-cis and trans-2-methoxy-1-(3-pyridyl)cyclohexanol (2 g, 10 mmol), toluene and phosphorus pentoxide (3.4 g, 24 mmol) was heated at reflux for 5 hours. The mixture was then filtered and the precipitate was portioned between 2M sodium hydroxide solution (80 ml) and diethyl ether (25 ml). The aqueous layer was extracted with ether (3×25 ml) and the combined organic extracts were dried over sodium sulphate. Concentration in vacuo afforded a crude oil which was purified by flash chromatography to give 2-(3-pyridyl)-cyclohexanone (0.7 g, 4 mmol).

REFERENCE EXAMPLE 5

To a solution of 2.5M n-butyl lithium in hexane (13.2 ml, 33 mmol) at −78° C. (was added diethyl ether (15 ml) followed by a solution of 3-bromopyridine (4.7 g, 30 mmol) in ether (90 ml) over a period of 10 minutes. After 1 hour at −78° C. a solution of (±)-2-methoxycyclohexanone (3.84 g, 30 mmol) in ether (20 ml) was added dropwise during 10 minutes. After 2 hours at −78° C. and 30 minutes at 0° C. the reaction mixture was warmed to 20° C. and then poured onto ice (150 g). The mixture was extracted with ether (2×50 ml) and then the combined organic extracts were extracted with 1N hydrochloric acid (50 ml). This aqueous extract was washed with ether (20 ml) and then treated with 2M sodium hydroxide solution (25 ml) and extracted with ether (3×100 ml). The organic extracts were combined, washed with brine then dried over anhydrous sodium sulphate. Concentration in vacuo afforded (±)-2-methoxy-1-(3-pyridyl)-cyclohexanol (5.0 g, 24 mmol) as a 4:1 mixture of cis and trans isomers; N.M.R. (CDCl$_3$), 1.2–2.14 (c), 2.24–2.44 (m), 2.90–3.28 (c); 3.48–3.60 (m), 7.18–7.30 (m); 7.78–7.96 (m); 8.40–8.48 (m); 8.62–8.72 (m); 8.78–8.82 (m).

EXAMPLE 2

Compound B

A solution of (±)-2-(3-quinolinyl)cyclohexanone (0.78 g, 3.5 mmol) in tetrahydrofuran (10 ml) at −5° C. was treated with potassium t.-butoxide (0.43 g, 3.9 mmol) in one portion. After 25 minutes at −5° C. the deep red mixture was treated dropwise during 1 minute with a solution of methyl isothiocyanate (0.28 g, 3.9 mmol) in tetrahydrofuran (2 ml). After 4 hours at 0° C. the reaction mixture was partitioned between saturated aqueous ammonium chloride solution (50 ml) and chloroform (50 ml). The aqueous layer was extracted again with chloroform (50 ml). The combined organic extracts were then dried over sodium sulphate and concentrated in vacuo (20° C.; 14 mmHg) to give a crude oil which was purified by flash chromatography over silica gel eluting with ethyl acetate to give (±)-N-methyl-2-oxo-1-(3-quinolinyl)cyclohexanecarbothioamide (0.1 g, 0.33 mmol), m.p. 235°–236° C. N.M.R. (CDCl$_3$) 1.7–2.18 (c, 4H), 2.46–2.64 (m, 2H) 2.72–2.90 (m, 1H), 2.96–3.16 (m, 1H), 3.16–3.22 (d, 3H), 7.50–7.62 (ddd, 1H), 7.66–7.76 (ddd, 1H), 7.76–8.02 (dd, 1M), 8.0 (d, 1M), 8.04–8.12 (dd, 1H), 8.78–8.80 (d, 1H), 8.92–9.18 (broad singlet, 1H). Calculated for $C_{17}H_{18}N_2OS$:

C,68.4; H, 6.08; N, 9.4; S, 10.7%: Found C, 68.0; H, 5.8; N, 9.0; S, 10.4%.

REFERENCE EXAMPLE 6

A solution of (±)-trans-1-[3-quinolinyl)-bromomethyl] cyclopentanol (1.1 g, 3.6 mmol) in tetrahydrofuran (20 ml) at 0° C. was treated, dropwise during 2 minutes, with a solution of silver perchlorate (893 mg, 4.3 mmol) in tetrahydrofuran (5 ml). After 1 hour at 0° C. a mixture of saturated brine solution (20 ml) and saturated aqueous sodium bicarbonate solution (20 ml) was added to the reaction mixture. Ethyl acetate (40 ml) was then added and the resulting mixture was filtered through diatomaceous earth. The aqueous layer was removed and extracted with ethyl acetate (50 ml). The combined organic extracts were washed with brine (30 ml), dried over sodium sulphate then concentrated in vacuo to afford (±)-2-(3-quinolinyl)cyclohexanone (0.8 g, 3.5 mmol) as an oil which solidified on standing, melting point 114°–115° C. N.M.R. (CDCl$_3$) 1.72–2.68.(c, 8H) 3.74–3.88 (dd, 1H), 7.46–7.56 (ddd, 1H), 7.62–7.70 (ddd, 1H), 7.72–7.82 (dd, 1H), 7.88–7.96 (d, 1H), 8.04–8.12 (d, 1H), 8.68 (d, 1H).

REFERENCE EXAMPLE 7

A mixture of 3-cyclopentylidenemethylquinoline (3 g, 14 mmol), water (100 ml), dimethyl sulphoxide (50 ml), acetone (100 ml) and concentrated sulphuric acid (3.4 ml, 35 mmol) at 5° C. was treated with 1,3-dibromo-5,5-dimethylhydantoin (4.0 g, 14 mmol). After 5 minutes at 5° C. the mixture was stirred for 2 hours at 20° C. The mixture was filtered and washed with ethyl acetate (2×50 ml). The aqueous phase was then treated with saturated aqueous sodium bicarbonate solution (50 ml) and extracted with ethyl acetate (100 ml). The organic phase was then washed with water (50 ml) and brine (50 ml) then dried over sodium sulphate. Concentration in vacuo afforded a crude oil which was purified by flash chromatography eluting with a mixture of diethyl ether and hexane (50:50) and then ether. The product so obtained was then recrystallized from cyclohexane to give (±)-trans-1-[(3-quinolinyl)bromomethyl]cyclopentanol (1.1 g, 3.6 mmol). N.M.R. 1.44–1.85 (c, 4H), 1.8–2.06 (c, 4H) 5.06 (s, 1H), 7.44–7.56 (ddd, 1H), 7.60–7.72 (ddd, 1H), 7.74–8.02 (dd, 1H) 8.04–8.12 (dd, 1H), 8.38–8.40 (d, 1H), 9.0 (d, 1H).

REFERENCE EXAMPLE 8

A solution of 2-chloro-3-cyclopentylidenemethylquinoline (7.6 g, 31.3 mmol) in glacial acetic acid (80 ml) at 60° C. was treated with zinc powder (4.0 g, 62.6 mmol). After stirring at 60° C. for 3 hours, the reaction mixture was cooled and then treated dropwise with 2M aqueous sodium hydroxide solution (330 ml); the temperature being kept below 20° C. throughout. The resulting mixture was then extracted with ethyl acetate (2×250 ml). The combined organic extracts were dried over sodium sulphate then concentrated in vacuo (30° C., 14 mm Hg) to give a crude red oil (8 g) which was extracted with hot pentane (2×200 ml). Concentration of the combined extracts in vacuo (20° C., 14 mm Hg) afforded 3-cyclopentylidenemethylquinoline (4 g, 31 mmol) which was used without further purification N.M.R. (CDCl$_3$) 1.6–1.96 (m, 4H); 2.5–2.72 (m, 4H); 6.50 (m, 1H), 7.46–7.58 (ddd, 1H) 7.60–7.68 (ddd, 1H), 7.76–7.80 (dd, 1H); 8.0–8.08 (c, 2H).

REFERENCE EXAMPLE 9

A suspension of cyclopentyltriphenylphosphonium bromide (4.1 g, 10 mmol) in tetrahydrofuran (50 ml) at 0° C. was treated with potassium t.-butoxide (1.1 g, 10 mmol) portionwise during 5 minutes. After 1 hour at 0° C. the deep red mixture was treated with 2-chloroquinoline-3- carbaldehyde (1.9 g, 10 mmol).

After 4 hours at 0° C. hexane (250 ml) followed by brine (50 ml) was added to the reaction mixture. The organic layer was removed and dried over sodium sulphate. After concentration in vacuo (30° C., 14 mm Hg) the crude oil was recrystallized from hexane to give 2-chloro-3-cyclopentylidenemethylquinoline (1.7 g, 7 mmol) m.p. 84°–86° C.; N.M.R. (CDCl$_3$); 1.64–1.90 (m, 4H); 2.44–2.66 (m, 4H); 6.52 (m, 1H); 7.44–7.56 (ddd, 1H); 7.58–7.68 (ddd, 1H); 7.70–7.78 (dd, 1H); 7.92–8.00 (dd, 1H); 8.04 (s, 1H). Calculated for C$_{15}$H$_{14}$ClN, C, 73.9; 14.11; Cl 14.5%; Found C, 74.3; H 5.8; Cl, 14.6, N, 5.7%.

REFERENCE EXAMPLE 10

A mixture of 3:1-cis:trans- (±)-2-methoxy-1-(3-quinolinyl)cyclohexan-1-ol (1.35 g, 5.3 mmol) and 40% w/v sulphuric acid (25 ml) was refluxed for 1 hour. The cooled mixture was basified with 1.0M sodium carbonate solution (200 ml) and the mixture extracted with ethyl acetate (3×125 ml). The combined organic extracts were washed with brine (30 ml) then dried over sodium sulphate. Concentration in vacuo afforded a crude oil (1.4 g) which was recrystallized from a 4:1 mixture of hexane and ethyl acetate (20 ml) to give (±)-2-(3-quinolinyl)cyclohexanone (0.53 g, 2.3 mmol), melting point 114°–115° C.

REFERENCE EXAMPLE 11

A solution 2.5M n-butyllithium in hexane (18 ml) in ether (30 ml) at −78° C. was treated dropwise with a solution of 3-bromoquinoline (4.7 g, 22.5 mmol) in ether (30 ml). After 1 hour at −78° C. a solution of (±)-2-methoxycyclohexanone (5.8 g, 45 mmol) in ether (30 ml) was added dropwise during 35 minutes to the reaction mixture, which was maintained at −78° C. for 2 hours then at 0° C. for 1 hour and then warmed to 20° C. during 1 hour. The reaction mixture was poured onto ice (50 g) and water (50 ml) and the resulting aqueous layer extracted with ether (3×50 ml). The combined organic extracts were treated with 2N HCl (75 ml) and the organic phase discarded. The aqueous layer was washed with ether (2×30 ml) then basified with 2N sodium hydroxide (75 ml). The aqueous layer was then extracted with ether (4×50 ml). The combined organic extracts were washed with brine (30 ml), dried over sodium sulphate and then concentrated in vacuo to afford a crude oil which was recrystallized from a 4:1 mixture of hexane and ethyl acetate (60 ml) to give a 3:1 mixture of (±)-cis and trans 2-methoxy-1-(3-quinolinyl-cyclohexan-1-ol (3.2 g, 12 mmol), melting point 114°–115° C. H n.m.r. (CDCl$_3$) essential features 3.06 (singlet, trans- OMe), 3.12 (singlet, cis- OMe).

EXAMPLE 3

Compound C

A stirred solution of (±)-2-(3-pyridyl)cycloheptanone (1.0 g, 5.3 mmol) in anhydrous tetrahydrofuran (10 ml) under argon at −5° C. was treated with potassium t-butoxide (0.65 g, 5.8 mmol).

After 25 minutes at −5° C. a solution of methyl isothiocyanate (0.42 g, 5.8 mmol) in tetrahydrofuran (1 ml) was added during 2 minutes.

After 3 hours at −5° C. the solution was warmed to 20° C. during 3 hours and then poured into a saturated aqueous ammonium chloride solution (50 ml). The mixture was extracted with chloroform (2×50 ml). The combined extracts were dried over sodium sulphate then concentrated in vacuo to afford a crude oil (1.7 g) which was purified by flash chromatography, eluting with a mixture of ethyl acetate and hexane (9:1) to afford (±)-N-methyl-2-oxo-1-(3-pyridyl)cycloheptanecarbothioamide (530 mg, 2.0 mmol), melting point 144°–146° C; N.M.R. (CDCl$_3$); 1.25–2.05 (C, 6H); 2.24–2.42 (m, 1H); 2.58–2.74 (m, 1H); 2.76–2.94 (m, 1H); 3.14 (d, 3H); 3.36–3.54 (m, 1H); 7.22–7.32 (m, 1H); 7.58–7.64 (m, 1H); 8.42–8.54 (m, 2H); 8.54–8.62 (broad singlet, 1H). Found C, 63.9; H, 6.9; N, 10.6; s, 12.4%; C requires C, 64.1; H, 6.9; N, 10.7; S, 12.2%.

REFERENCE EXAMPLE 12

A stirred solution of (±)-trans-1-[(3-pyridyl)-bromomethyl]cyclohexanol (4.2 g, 15.5 mmol) in tetrahydrofuran (50 ml) at 0° C. was treated dropwise with a solution of silver perchlorate (3.9 g, 18.8 mmol) in tetrahydrofuran (20 ml) during 20 minutes. After 3 hours at 0° C. the mixture was treated with saturated aqueous brine solution (50 ml) followed by saturated aqueous sodium bicarbonate solution (50 ml). Ethyl acetate (50 ml) was then added and the mixture was filtered through diatomaceous earth. The organic phase was removed and the aqueous phase was extracted with ethyl acetate (50 ml). The combined organic extracts were washed with brine (20 ml) then dried over sodium sulphate. Concentration in vacuo followed by flash chromatography over silica gel eluting with ethyl acetate afforded (±)-2-(3-pyridyl)cycloheptanone (0.4 g, 2.1 mmol) as an oil. N.M.R. (CDCl$_3$); 1.32–2.20 (m, 8H); 2.56–2.70 (m 2H), 3.34–3.86 (dd, 1H); 7.22–7.32 (m, 1H), 7.54–7.62 (m, 1H), 8.4–8.54 (m, 2H). Found C, 76.4; H, 8.3; N, 7.3%: C$_{12}$H$_{15}$NO requires C, 76.2; H, 8.0; N, 7.4%.

REFERENCE EXAMPLE 13

A mixture of 3-cyclohexylidenemethylpyridine (1.6 g, 9.3 mmol) and 1M sulphuric acid (25 ml) at −10° C. was added 1,3-dibromo-5,5-dimethylhydantoin (3.2 g, 11 mmol) during 15 minutes. After stirring at 0° C. for 1 hour the reaction mixture was filtered then washed with ethyl acetate (20 ml). The aqueous phase was treated with sodium bicarbonate (5 g) and then extracted with a 2:1 mixture of hexane and ethyl acetate (20 ml), and then ethyl acetate (20 ml). The combined organic extracts were washed with water (3×5 ml) then with brine (5 ml) and dried over sodium sulphate. Concentration in vacuo (30° C.; 14 mm Hg) afforded a crude oil (1.5 g) which was purified by flash chromatography over silica gel eluting with ethyl acetate to give (±)-trans-1-[(3-pyridyl)bromomethyl]cyclohexanol (0.5 g, 1.8 mmol) m.p. 120°–122° C. N.M.R. (CDCl$_3$) 1.02–2.12 (c, 11H), 4.96 (s, 1H), 7.22–7.34, (m, 1H), 7.90–8.02 (m, 1H), 8.46–8.56 (dd, 1H), 8.56–8.62 (d, 1H) Found C, 53.4; H, 6.0; Br, 29.5; N, 5.1: C$_{12}$H$_{15}$BrNO requires C, 53.4; H, 6.0; Br, 29.6; N, 5.2.

EXAMPLE 4

Compounds D and E

A stirred solution of (±)-N-methyl-2-(3-pyridyl)-cyclohexanecarbothioamide (1.7 g, 6.9 mmol) in methanol (4 ml) at 0° C. was treated with sodium borohydride (262 mg, 6.9 mmol). After 10 minutes at 0° C. the mixture was warmed to 20° C. and a solution formed. It was then cooled to 0° C. and stirred for a further 40 minutes. The reaction mixture was then treated with brine (10 ml) and water (30 ml) and extracted with ethyl acetate (2×50 ml). The combined organic extracts were washed with brine (10 ml) then dried over anhydrous sodium sulphate. After concentration in vacuo (30° C.;14 mmHg) the product was fractionally recrystallised from cyclohexane: ethyl acetate (6:1) (10 ml) to afford (±)-trans-N-methyl-2-hydroxy-1-(3-pyridyl)cyclohexanecarbothioamide (1.4 g, 5.6 mmol) [m.p. 171°–172° C. N.M.R. (CDCl$_3$) 1.24–2.02 (m, 6H); 2.08–2.28 (dt, 1H) 2.46–2.60 (m, 1H); 3.06–3.12 (d, 3H); 3.54–3.78 (br.s, 1H); 4.70–4.86 (m, 1H); 7.26–7.28 (m, 1H); 7.44–7.70 (br.s, 1H); 8.20–8.28 (dt,1H); 8.48–8.58 (dd, 1H); 8.92–8.96 (d, 1H). Calculated for C$_{13}$H$_{18}$N$_2$OS; C, 62.4; H, 7.3; N, 11.2; S, 12.8 Found; C, 62.3; H, 7.3; N, 11.4; 12.7.] and (±)-cis-N-methyl-2-hydroxy-1-(3-pyridyl)cyclohexanecarbothioamide (0.2 g, 0.8 mmol). [m.p. 169°–172° C. NMR (CDCl$_3$) 1.32–2.06 (complex, 7H); 2.88–3.04 (m, 1H); 3.22–3.30 (d, 3H); 4.36–4.48 (dd, 1H); 5.46–6.06 (broad singlet, 14); 7.14–7.26 (m, 1H); 7.81–7.92 (m, 1H); 8.16–8.24 (dd, 1H); 8.52–8.60 (m, 1H). Calculated for C$_{13}$H$_{18}$N$_2$OS; C, 62.4; H, 7.3; N, 11.2; S, 12.8. Found C, 62.0; H, 7.3; N, 11.1; S, 12.7.]

EXAMPLE 5

Compound F

A suspension of (±)-N-methyl-2-oxo-1-(3-pyridyl) cyclohexanecarbothioamide (370 mg, 1.5 mmol) in pyridine (3 ml) at 20° C. was treated with hydroxylamine hydrochloride (210 mg, 3.0 mmol). After 4 days at 20° C. the mixture was poured into water (50 ml) which was then extracted with ethyl acetate (2×20 ml). The combined organic extracts were washed successively with water (10 ml), and then brine (10 ml) then dried over anhydrous sodium sulphate. After concentration in vacuo (30° C.; 14 mmHg) the crude product was recrystallized from propan-2-ol to give (±)-anti-N-methyl-2-hydroxyimino-1-(3-pyridyl)cyclohexanecarbothioamide (220 mg, 0.84 mmol), m.p. 181°–183° C., N.M.R. (D6-dimethylsulphoxide) 1.26–1.82 (m, 4H); 2.08–2.38 (m, 2H); 2.86–3.20 (m, 5H); 7.24–7.34 (m, 1H); 7.58–7.68 (m, 1H); 8.32–8.40 (m, 1H); 8.42–8.50 (m, 1H); 9.44–9.60 (broad multiplet, 1H) 10.90 (singlet, 1H)s. Calculated for C$_{13}$H$_{17}$N$_3$OS, C, 59.3; H, 6.5; N, 15.96%; S, 12.17; Found: C, 59.7; H, 6.63; N, 16.0; S, 12.3%.

EXAMPLE 6

Compound G

A suspension of (±)-N-methyl-2-oxo-1-(3-pyridyl)-cyclohexanecarbothioamide (0.5 g, 2 mmol) in pyridine (5 ml) at 20° C. was treated with O-methylhydroxylamine hydrochloride (0.34 g, 4 mmol). After stirring for 48 hours at 20° C. the mixture was treated with another portion of O-methylhydroxylamine hydrochloride (0.68 g, 8 mmol) and then warmed to 40° C. After 2 hours the solution was poured into water (50 ml) and the resulting mixture was extracted with ethyl acetate (3×50 ml). The combined organic extracts were washed with water (20 ml) then dried over sodium sulphate. Concentration in vacuo afforded a crude oil (0.6 g) which was recrystallized from isopropanol to give (±)-anti-N-methyl-2-methoxyimino-1-(3-pyridyl)cyclohexanecarbothioamide (0.3 g, 1.1 mmol), melting point 150°–151° C. H n.m.r. (CDCl$_3$) 1.5–2.06 (C, 4H), 2.14–2.26 (C, 2H), 2.74–3.02 (C, 2H), 3.18–3.24 (d, 3H), 3.84 (s, 3H), 7.16–7.28 (m, 1H), 7.56–7.64 (m, 1H), 8.42–8.48 (m, 1H), 8.48–8.70 (C, 2H); found : C, 60.1; H, 6.8; N, 14.9; s, 11.6% C requires : C, 60.6; H, 6.9; N, 15.2; S, 11.6%.

EXAMPLE 7

Compound H

A solution of (±)-N-methyl-2-oxo-(3-pyridyl)cyclohexanecarbothioamide (0.5 g, 2 mmol) in pyridine (5 ml) at 60° C. was treated with O-benzylhydroxylamine hydrochloride (0.65 g, 4 mmol) and the resulting mixture was then stirred for 24 hours at 60° C. The reaction mixture was partitioned between water (50 ml) and ethyl acetate (25 ml) and the aqueous layer was then extracted with ethyl acetate (2×25 ml). The combined organic extracts were washed with brine (50 ml) then dried over magnesium sulphate. recrystallised from ethyl acetate to give (±)-anti-N -methyl-2-benzyloxyimino-1-(3-pyridyl)cyclohexanone (0.57 g, 1.6 mmol), melting point 128°–130° C. H n.m.r. (CDCl$_3$) 1.48–2.15 (c, 4H), 2.16–2.40 (m, 2H), 2.8–2.96 (m, 2H), 2.96–3.04 (d, 3H), 5.02–5.08 (s, 2H), 7.12–7.22 (c, 3H), 7.32–7.44 (c, 3H), 7.44–7.56 (m, 2H), 8.16–8.38 (broad singlet, 1H), 8.38–8.52 (c, 2H). Found: C, 67.7; H, 6.5; N, 11.9; S, 9.0% $C_{20}H_{23}N_3OS$ requires C, 68.0; H, 6.6; N, 11.9; S, 9.1%.

EXAMPLE 8

Compound I

A solution of (±)-N-methyl-2-oxo-1-(3-quinolinyl)-cyclohexanecarbothioamide (0.4 g, 1.3 mmol) in pyridine (5 ml) at 20° C. was treated with hydroxylamine hydrochloride (0.19 g, 2.3 mmol). After 24 hours at 20° C. the solution was partitioned between ethyl acetate (75 ml) and water (75 ml). The aqueous layer was extracted with ethyl acetate (3×75 ml) and the combined organic extracts were washed with water (15 ml) then dried over sodium sulphate. Concentration in vacuo afforded a crude oil (0.55 g) which was recyrstallized from isopropanol to give (±)-anti-N-methyl-2-hydroxyimino-(3-quinolinyl)cyclohexanecarbothioamide (0.25 g, 0.8 mmol), melting point 185°–186° C. H n.m.r. (CDCl$_3$) 1.48–2.46 (c, 6H), 2.96–3.08 (m, 1H), 3.08–3.18 (d, 3H), 3.18–3.38 (m, 1H), 7.44–7.56 (dt, 1H), 7.60–7.70 (dt, 1H), 7.70–7.80 (dd, 1H), 7.96–8.06 (m, 2H), 8.52–8.68 (broad multiplet) 10.90 (s, 1H). Found : C, 64.8; H, 6.1; N, 13.3; S, 9.9%; $C_{17}H_{19}N_3OS$ requires C, 65.2; H, 6.1; N, 13.4; S, 10.2%.

EXAMPLE 9

A solution of (2S,2'S)-anti-2-(methoxymethyl) -1-[2'-(3-quinolyl)-2'-methylthiocarbamoylcyclohexylideneamino]pyrrolidine (117 mg, 0.28 mmol; prepared in Example 10) in acetone (1 ml), water (0.8 ml) and glacial acetic acid (0.5 ml) was heated at 60° C. for 13 hours. The reaction mixture was cooled to 20° C. and the precipitated solid was filtered off and washed with acetone (2×1 ml). Recrystallization from methanol afforded the (S)-isomer of N-methyl-2-oxo-1-(3-quinolinyl)cyclohexanecarbothioamide (41 mg, 0.14 mmol), m.p. 256°–257° C. H n.m.r. (CDCl$_3$) 1.71–2.08 (c, 4H); 2.57 (m, 2H); 2.8 (m, 1H); 3.08 (m, 1H); 3.17 (d, 3H); 7.55 (dt, 1H); 7.66–7.82 (c, 2H); 7.99 (d, 1H); 8.08 (d, 1H); 8.79 (d, 1H); 8.94–9.14 (broad singlet, 1H). Found C, 68.9; H, 6.3; N, 9.3% $C_{17}H_{18}N_2OS$ requires C, 68.4; H, 6.1; N, 9.4%).

EXAMPLE 10

Compound J

A vigorously stirred solution of a 50:50 mixture of 2S-(+)-2-(methoxymethyl)-1-[2-(3-quinolinyl)-cyclohexylideneamino]pyrrolidine and 2S-(-)-2-(methoxymethyl)-1-[2-(3-quinolinyl) -cyclohexylideneamino]pyrrolidine (2.6 g, 7.8 mmol) in tetrahydrofuran (30 ml) at −78° C. was treated with a 1.6M solution of n-butyllithium in hexane (5.9 ml, 9.4 mmol). After 30 minutes at −78° C. the reaction mixture was warmed to 0° C. and diethylether (30 ml) was added. After 15 minutes at 0° C. the reaction mixture was cooled to −78° C. then treated with methyl isothiocyanate (730 mg, 10 mmol). The reaction mixture was stirred at −78° C. for 1 hour then warmed slowly to 20° C. over 3 hours. Saturated aqueous ammonium chloride solution (20 ml) was added to the solution, followed by the addition of ethyl acetate (50 ml). The aqueous layer was extracted with ethyl acetate (2×25 ml) and the combined organic extracts were dried over sodium sulphate. Concentration in vacuo afforded a crude oil which when treated with cyclohexane (40 ml) precipitated a crude solid. Recrystallization from a 5:1 mixture of cyclohexane and ethyl acetate gave (2S,2'S)-anti-2-(methoxymethyl)-1-[2'-(3-quinolinyl)-2'-methylthiocarbamoylcyclohexylideneamino]pyrrolidine (1.1 g, 2.7 mmol), melting point 166°–168° C. H n.m.r. (CDCl$_3$) 1.48–2.10 (c, 8H); 2.16–2.76 (c, 4H); 3.14 (d, 3H), 3.17–3.8 (c, 3H); 3.41 (s, 3H); 3.49 (d, 2H); 7.50 (dt, 1H); 7.66 (dt, 1H); 7.78 (dd, 1H); 8.00–8.10 (c, 2H); 8.86 (d, 1H); 10.7 (broad singlet, 1H). Found C, 67.6%; H, 7.5%; N, 13.6%; S, 7.8% $C_{23}H_{30}N_4OS$ requires C, 67.3; H, 7.4; N, 13.7; S, 7.8%.

The absolute configuration wa confirmed by X-ray crystallography.

REFERENCE EXAMPLE 14

A mixture of (±)-2-(3-quinolinyl)cyclohexanone (0.5 g, 2.2 mmol), (S)-(−)-1-amino-2-(methoxymethyl)pyrrolidine ('SAMP')(0.28 g, 2.2 mmol) and p-toluenesulphonic acid (10 mg) was refluxed in toluene (15 ml) for 2.5 hours. The toluene was removed in vacuo (40° C./14 mmHg,) to give a crude oil which was partitioned between water (20 ml) and ethyl acetate (25 ml). The aqueous layer was extracted with ethyl acetate (2×25 ml) and the combined organic extracts were dried over sodium sulphate then concentrated in vacuo to give (2S)-(+)-2-(methoxymethyl) -1-[2-(3-quinolinyl)cyclohexylideneamino]pyrrolidine and (2S)-(−)-2-(methoxymethyl)-1-[2-(3-quinolinyl)cyclohexylideneamino]pyrrolidine as a 50:50 mixture of diastereoisomers (0.69 g, 2 mmol).

EXAMPLE 11

A solution of (2R)-anti-2-(methoxymethyl) -1-[2'-(3-quinolinyl)-2'-methylthiocarbamoylcyclohexylideneamino]pyrrolidine (122 mg, 0.3 mmol; prepared in Example 12) in acetone (1 ml), water (0.8 ml) and glacial acetic acid (0.5 ml) was heated at 60° C. for 13 hours. The reaction mixture was cooled to 20° C. and the precipitated solid was filtered off and washed with acetone (2×1 ml). Recrystallization from methanol afforded the (R)-isomer, by inference, of N-methyl-2-oxo-1-(3-quinolinyl)cyclohexanecarbothioamide (39 mg, 0.13 mmol), m.p. 255°–256° C. H n.m.r. (CDCl₃) 1.71–2.08 (c, 4H); 2.57 (m, 2H); 2.8 (m, 1H); 3.08 (m, 1H); 3.17 (d, 3H); 7.55 (dt, 1H); 7.66–7.82 (c, 2H); 7.99 (d, 1H); 8.08 (d, 1H); 8.79 (d, 1H); 8.94–9.14 (broad singlet, 1H). Found C, 68.1; H, 6.0; N, 9.4%; $C_{17}H_{18}N_2OS$ requires C, 68.4; H, 6.1; N, 9.4%.

EXAMPLE 12

A solution of a 50:50 mixture of 2(R)-(+)-2-(methoxymethyl)-1-[2-(3-quinolinyl)cyclohexylideneamino]pyrrolidine and 2 (R)-(−)-2-(methoxymethyl)-1-[2-(3-quinolinyl)cyclohexylideneamino]pyrrolidine (2.6 g, 7.8 mmol) in tetrahydrofuran (30 ml) was added dropwise to a solution of 1.6M n-butyllithium in hexane (5.2 ml) containing tetrahydrofuran (20 ml) at −78° C. After 1.5 hours at −78° C. the reaction mixture was treated with a solution of methyl isothiocyanate (0.68 g, 9.3 mmol). After 15 minutes at −78° C. the solution was warmed slowly to 0° C. over 2 hours. After 30 minutes at 0° C. aqueous saturated ammonium chloride (30 ml) was added to the reaction mixture which was extracted with chloroform (2×50 ml). The combined organic extracts were washed with brine (20 ml) then dried over sodium sulphate. Concentration in vacuo afforded a crude oil (3.2 g) which was, recrystallized from a 5:1 mixture cyclohexane and ethyl acetate to give (2R)-anti-2-(methoxymethyl)-1-[2'-(3-quinolinyl)-2'-methylthiocarbamoylcyclohexylideneamino]pyrrolidine (0.67 g, 1.6 mmol) m.p. 163°–165° C. H n.m.r. (CDCl₃) 1.48–2.10 (c, 8H); 2.16–2.76 (c, 4H); 3.14 (d, 3H); 3.17–3.8 (c, 3H); 3.41 (s, 3H); 3.49 (d, 2H); 7.50 (dt, 1H); 7.66 (dt, 1H); 7.78 (dd, 1H); 8.00–8.10 (c, 2H); 8.86 (d, 1H); 10.7 (broad singlet, 1H). Found C, 67.4; H, 7.5; N, 13.6; S, 7.7 $C_{23}H_{30}N_4OS$ requires C, 67.3; H, 7.4; N, 13.7; S, 7.8%.

By inference, this was the (2'R)-isomer.

REFERENCE EXAMPLE 15

A mixture of (±)-2-(3-quinolinyl)cyclohexanone (1.75 g, 7.8 mmol), (R)-(+)-1-amino-2-(methoxymethyl)pyrrolidine ('RAMP')(1.0 g, 7.8 mmol) and p-toluenesulphonic acid (20 mg) was refluxed in toluene (40 ml) for 1.5 hours using a Dean-Stark apparatus. The toluene was removed in vacuo at 40° C./14 mmHg and then at 20° C./0.1 mmHg to give a crude oil (2.6 g) containing (2R)-(+)-2-(methoxymethyl)-1-[2-(3-quinolinyl)cyclohexylideneamino]pyrrolidine and hexylideneamino]pyrrolidine as a 50:50 mixture of diastereoisomers. This mixture was used as such without further purification.

EXAMPLE 13

Compound K

A 2.5M solution of n-butyllithium in hexane (47 ml) was added dropwise to a stirred solution of (2S)-2-methoxymethyl-1-[2-(3-pyridyl)-cyclohexylideneamino]pyrrolidine (50:50 mixture of diastereoisomers) (30.73 g) in dry tetrahydrofuran (410 ml) at −75° C. under argon during 15 minutes, to give a dark red solution. After 30 minutes, a solution of methyl isothiocyanate (8.63 g) in tetrahydrofuran (65 ml) was added during 10 minutes. The solution was allowed to warm to 0° C. during 45 minutes, maintained at this temperature for 1 hour and then at 20° C. for 1 hour, giving a yellow solution. This solution was quenched with saturated aqueous ammonium chloride solution (270 ml). The organic layer was separated and the aqueous layer extracted with ether (3×50 ml). The combined extracts were washed with brine (2×25 ml), dried over magnesium sulphate and evaporated (40° C./0.2 mmHg) to give crude 2'-methylthiocarbamoylcyclohexylideneamino]pyrrolidine, a semi-crystalline oil (39.81 g).

By inference, this was the (2'S)-isomer.

EXAMPLE 14

A solution of (2S)-anti-2-methoxymethyl -1-[2'-(3-pyridyl)-2'-methylthiocarbamoylcyclohexylideneamino]pyrrolidine (prepared in Example 13), in 2M aqueous hydrochloric acid (400 ml) was stirred at 60° C. for 12 hours. The solution was washed with methylene chloride (3×150 ml). The aqueous phase was brought to pH 8 with 2M aqueous sodium hydroxide solution. The precipitate was extracted into methylene chloride (500 ml +3×150 ml). The combined extracts were washed with water (3×50 ml), dried over magnesium sulphate and evaporated. The residual solid was washed with ethyl acetate (50 ml) and recrystallized from methanol to give the (S)-isomer, by inference, of N-methyl-2-oxo-1-(3-pyridyl)cyclohexanecarbothioamide, colorless crystals (12.04 g), m.p. 193°–194° C., $[\alpha]^{30}$ −83° (CHCl₃).

REFERENCE EXAMPLE 16

By proceeding in a similar manner to that hereinbefore described in Reference Example 15, there was prepared (2S)-2-methoxymethyl-1-[2-(3-pyridyl)cyclohexylideneamino]pyrrolidine (50:50 mixture of diastereoisomers), a yellow oil.

EXAMPLE 15

By proceeding in a similar manner to that hereinbefore described in Example 7, there was prepared the (S)-isomer by inference of anti-N-methyl-2-benzyloxyimino-1-(3-pyridyl)cyclohexanecarbothioamide, colorless crystals, m.p.129°–130° C., $[\alpha]^{28}$ −59.4° (CHCl₃), from N-methyl-2-oxo-1-(3-pyridyl)cyclohexanecarbothioamide (prepared in Example 14).

EXAMPLE 16

Compound L

A stirred suspension of (±)-N-methyl-2-oxo-1-(3-pyridyl)cyclohexanecarbothioamide (0.5 g) and 2-dimethylaminoethoxyamine hydrochloride (0.37 g) in ethanol (5 ml) and pyridine (1 ml) was refluxed for 24 hours. The reaction mixture was evaporated and the residual gum dissolved in water (15 ml) and washed with chloroform 4×7.5 ml). The aqueous phase was brought to pH 14 with 2M aqueous sodium hydroxide solution and then extracted with chloroform (4×10 ml). The combined extracts were dried over magnesium sulphate, and evaporated. The residual oil was triturated with water to give (±)-anti-N-methyl-2-(2-dimethylaminoethoxyimino) -1-(3-pyridyl)cyclohexanecarbothioamide, a colorless solid (0.55 g), m.p. 93°–95° C.

EXAMPLE 17

Compound M

A stirred suspension of (±)-N-methyl-2-oxo-1-(3-pyridyl)cyclohexanecarbothioamide (1.24 g) and 2- aminoethoxyamine dihydrochloride (0.78 g) in ethanol (12.5 ml) and pyridine (2.5 ml) was refluxed for 11 hours. The reaction mixture was evaporated and the residual gum dissolved in water (15 ml) and washed with chloroform (4×10 ml). The aqueous phase was brought to pH 14 with 2M aqueous sodium hydroxide solution and then extracted with chloroform (4×10ml). The combined extracts were dried over magnesium sulphate, and evaporated. The residual oil was purified by flash chromatography on silica eluting with chloroform/methanol/triethylamine: 95/5/2 to give a colorless oil (0.93 g). A solution of this oil (0.72 g) in ethanol (10 ml) was treated with a solution of citric acid (1.1 g) in ethanol (10 ml). Addition of ether precipitated a solid which was washed with further ether to give (±)-anti-N-methyl-2-(2-aminoethoxyimino)-1-(3-pyridyl)cyclohexanecarbothioamide citrate (1.15 g), a colorless solid, m.p. 68°–70° C.

EXAMPLE 18

Compounds N, O, P and Q

A stirred suspension of (±)-N-methyl-2-oxo-1-(3-pyridyl)cyclohexanecarbothioamide (2.48 g) and methyl aminooxyacetate (1.1 g) in ethanol (25 ml) and pyridine (5 ml) was refluxed for 24 hours. The solution was evaporated, the residue dissolved in chloroform (100 ml), and washed with water (3×75 ml). The chloroform phase was dried over magnesium sulphate and evaporated. The residual oil was purified by flash chromatography, eluting with ethyl acetate to give (±)-anti-N-methyl-2-methoxycarbonylmethoximino-1-(3-pyridyl) cyclohexanecarbothioamide (2.35 g), a colorless solid, m.p. 129°–131° C.

By proceeding in a similar manner, there were prepared (±)-anti-N-methyl-2-carbamoylmethoxyimino-1-(3-pyridyl)cyclohexanecarbothioamide, colorless solid, m.p. 168°–169° C., after purification by flash chromatography on silica, eluting with ethyl acetate, followed by trituration with ether; (±)-anti-N-methyl-2-(2,3-dihydroxypropoxyimino) -1-(3-pyridyl)cyclohexanecarbothioamide, a yellow gum, after purification by flash chromatography on silica eluting with ethyl acetate/methanol:9/1; (±)-anti-N-methyl-2-(2-hydroxyethoxyimino)-1-(3-pyridyl)cyclohexanecarbothioamide, a yellow oil, after purification by flash chromatography on silica eluting with ethyl acetate.

EXAMPLE 19

Compound R

A vigorously stirred solution of 2-(6-chloropyrid-3-yl)cyclohexanone (0.36 g 1.7 mmol) in anhydrous tetrahydrofuran (10 ml) under argon at −15° C. was treated with potassium t-butoxide (0.19 g, 1.7 mmol). The resulting mixture was stirred for 2 hours at room temperature before the addition of a solution of methyl isothiocyanate (0.12 g, 1.7 mmol) in dry tetrahydrofuran (2 ml). The mixture was stirred for a further 48 hours at room temperature, concentrated in vacuo and the residue treated with water (30 ml) and extracted with ethyl acetate (50 ml). The organic extract was dried over magnesium sulphate and then concentrated in vacuo (30° C.; 14 mmHg) to give a yellow oil which was purified by flash chromatography over silica gel eluting with ethyl acetate: hexane 4:6 to give (±)-N-methyl-2-oxo-1-(6-chloropyrid-3-yl) -cyclohexanecarbothioamide (0.25 g) m.p. 172°–3° C. NMR (CDCl$_3$) 1.64–2.14(m 4H); 2.4–2.65(m 2H); 2.7–2.8(m 2H); 3.14–3.16(d,3H); 7.26–7.34 (ddd,1H); 7.6–7.66(dd,1H); 8.2(d,1H); 8.84–9.06 (broad singlet, 1H). Calculated for C$_{13}$H$_{15}$ClN$_2$OS; C,55.2%; H,5.35%; N,9.91%, Cl,12.5%; Found C,55.3%; H,5.3%; N,9.8%;Cl,12.6%.

EXAMPLE 20

Compound S

A 33% w/v solution of methylamine in ethanol (5.7 ml) was added dropwise to a stirred solution of 2-(5-bromopyrid-3-yl)-2-methylthiothiocarbonylcyclohexanone (1.33 g, 3.86 mmol) in ethanol (25 ml) and dichloromethane (25 ml) at 0°–5° C. The solution was stirred at room temperature for 5 hours and concentrated in vacuo at 30°–35° C. The residue was purified by flash chromatography over silica gel eluting with ethyl acetate: hexane 4:6 to give (±)-N-methyl-2-oxo-1-(5-bromopyrid-3-yl) -cyclohexanecarbothioamide (0.57 g) m.p. 201°–3° C. NMR(CDCl$_3$) 1.68–2.16(m,4H); 2.46–2.6(m,2H); 2.66–2.8(m,2H); 3.17–3.17–3.19 (d,3H); 7.74–7.78(dd,1H); 8.38–8.39(d,1H), 8.58–8.59(d,1H); 8.8–9.0(broad singlet). Calculated for 47.7%; H,4.6%; N,8.6%. Found C, 48.2%; H,4.7%; N,8.5%.

REFERENCE EXAMPLE 17

To a solution of 2-(5-bromopyrid-3-yl)cyclohexanone (1.28 g, 5.05 mmol) in dry tetrahydrofuran (35 ml) at −40° C. was added portionwise with stirring potassium tert. butoxide (0.61 g, 5.4 mmol). The reaction mixture was stirred for 1 hour at −40° C. and a solution of carbon disulphide (0.5 ml) in dry tetrahydrofuran (5 ml) was added and the reaction mixture allowed to warm up to −20° C. over 20 minutes. A solution of methyl iodide (1.03 g) in dry tetrahydrofuran (5 ml) was added dropwise and the solution stirred at room temperature for 6 hours. The reaction mixture was concentrated in vacuo, treated with water (25 ml) and extracted with dichloromethane (2×25 ml). The extract was washed with water, dried over magnesium sulphate and concentrated to give 2-(5-bromopyrid-3-yl)-2-methylthiothiocarbonylcyclohexanone as an orange oil 1.33 g. NMR (CDCl$_3$) 1.6–2.1(m,4H); 2.26–2.35(m,2H); 2.6 (s,3H); 2.65–2.9(m.1H); 3.4–3.5(m,1H), 7.84–7.86(dd,1H); 8.54–8.6(dd,2H).

REFERENCE EXAMPLE 18

A solution of 3,5-dibromopyridine (30.45 g, 0.13 mol) in anhydrous ether (400 ml) was added dropwise to a stirred solution of n-butyllithium (1.6M in hexane, 88.3 ml) and anhydrous ether (40 ml) over 0.5 hours at −70° C. The pale yellow suspension was stirred at −70° C. for 1 hour, and a solution of 2-methoxycyclohexanone (16.5 g, 0.13 mol) in anhydrous ether (60 ml) was added dropwise. The reaction mixture was stirred at −70° C. for 2 hours and allowed to warm to room temperature. The reaction mixture was poured onto ice/water (1l); sodium chloride (50 g) was added and the ether layer separated. The aqueous layer was extracted with ether (2×200ml). The combined ether layers were extracted with 2N hydrochloric acid (2×250 ml). The acid extract was washed with ether (200 ml), basified with 4N aqueous sodium hydroxide solution at room temperature (pH11), sodium chloride (50 g) was added and the precipitated oil was extracted with ether (2×400 ml). The combined extracts were dried over magnesium sulphate and concentrated in vacuo to give 2-methoxy-1-(5-bromopyrid-3-yl)cyclohexanol (30.6 g). The cyclohexanol was added in small portions to stirred sulphuric acid (114 ml). The reaction exothermed to 50° C., but no external cooling was applied. When the addition was completed after 20 minutes the red/brown solution was stirred at room temperature for 4 hours. The reaction mixture was poured onto ice/water (11) and basified to pH8 with sodium carbonate. The product was extracted with ether (2×300 ml). The ether extracts were combined, dried with magnesium sulphate and evaporated to give a pale orange oil. The oil was purified by flash chromatography over silica gel eluting with hexane/ethyl acetate 6.4 to give 2-(5-bromopyrid-3-yl)cyclohexanone (15.1 g) m.p. 67°-9° C. NMR(CDCl$_3$). 1.6-2.1(m,4H); 2.1-2.4(m,2H); 2.4-2.6 (m,2H); 3.6-3.66(dd,1H); 7.6(s,1H); 8.18(s,1H); 8.38(s,1H).

EXAMPLE 21

Compounds T and U

By proceeding in a similar manner to that hereinbefore described in Example 1 but replacing methyl isothiocyanate by ethyl isothiocyanate there was prepared (±)-N-ethyl-2-oxo-1-(3-pyridyl)cyclohexanecarbothioamide, a colorless solid, m.p. 126°-130° C., after being purified by trituration with diethyl ether.

By proceeding in a similar manner to that hereinbefore described in Example 2 but replacing methyl isothiocyanate by ethyl isothiocyanate there was prepared (±)-N-ethyl-2-oxo-1-(3-quinolinyl) -cyclohexanecarbothioamide, m.p. 156°-158° C.

EXAMPLE 22

Compound W

A mixture of (±)-N-methyl-2-oxo-1-(3-quinolinyl)cyclohexanecarbothioamide (2.98 g, 10 mmol), 1,1-diethylhydrazine monohydrochloride (2.49 g., 20 mmol) and pyridine (15 ml) was stirred and heated at 65°-70° C. for 31 hours, further quantities of 1,1-diethylhydrazine monohydrochloride (2.49 g, 20 mmol) being added after 20 hours and 31 hours during this period. The reaction mixture was then diluted with di-isopropyl ether (20 ml) and pyridine (5 ml), stirred at 100°-150° C. for 52 hours under reflux, added to ice (100 g) and the pH of the mixture adjusted to 8 by the addition of sodium hydrogen carbonate. The crude product was extracted using dichloromethane (80 ml; 3×20 ml), the combined extracts washed with saturated brine solution (2×20 ml) and dried over a mixture of magnesium sulphate and charcoal. The solvent was removed in vacuo to give a brown gum, which was purified by flash chomatography over silica gel, using a mixture of toluene: acetone (9:1) as eluting solvent, followed by recrystallization twice from a mixture of petroleum ether (b.p. 60°-80° C.): diethyl ether (2:1). This procedure afforded (±)-N-anti-methyl-2-diethylhydrazono-1-(3-quinolinyl)cyclohexanecarbothioamide (1.00 g, 2.7 mmol) as a peach solid, melting point 117°-118° C.

NMR-(CDCl$_3$); 1.04-1.15 (t,6H), 1.60-1.90 (c,4H), 1.92-2.06(c,1H), 2.30-2.62 (qq,2H), 2.66-2.82 (m,3H), 2.82-2.98 (m,1H), 3.06-3.21 (dm,4H), 7.44-7.56 (m,1H), 7.60-7.79 (m,2H), 8.00-8.08 (m,2H), 8.84-8.88 (d,1H), 10.94-11.08 (broad singlet, 1H).

Microanalysis; found; C,68.3; H,7.6; N,15.2; S,9.0%. C requires; C,68.4; H,7.7; N 15.2; S,8.7%.

EXAMPLE 23

Compounds X to AK

By proceeding in a similar manner to that hereinbefore described in Example 7, there were prepared:

(±)-anti-N-methyl-2-benzyloxyimino-1-(3-quinolinyl)-cyclohexanecarbothioamide, m.p. 158°-160° C.;

(±)-anti-N-methyl-2-methoxyimino-1-(3-quinolinyl) cyclohexanecarbothioamide, m.p. 179°-181° C.;

(±)-anti-N-methyl-2-ethoxyimino-1-(3-quinolinyl)cyclohexanecarbothioamide, m.p. 190°-192° C.;

(±)-anti-N-methyl-2-butoxyimino-1-(3-quinolinyl)cyclohexanecarbothioamide, m.p. 165°-167° C.;

(±)-anti-N-methyl-2-(3-isopropylamino-2-hydroxypropoxyimino)-1-(3-quinolinyl)cyclohexanecarbothioamide, m.p. 50° C.;

(±)-anti-N-methyl-2-t.butoxyimino-1-(3-quinolinyl)cyclohexanecarbothioamide, m.p. 158°-160° C.;

(±)-anti-N-methyl-2-prop-2-enoxyimino-1-(3-quinolinyl)cyclohexanecarbothioamide, m.p. 162°-165° C.;

(±)-anti-N-methyl-2-naphth-2-ylmethoxyimino-1-(3-quinolinyl)cyclohexanecarbothioamide, m.p. 180°-183° C.;

(±)-anti-N-methyl-2-phenethyloxyimino-1-(3-quinolinyl)cyclohexanecarbothioamide, m.p. 145°-147° C.;

(±)-anti-N-methyl-2-naphth-1-ylmethoxyimino-1-(3-quinolinyl)cyclohexanecarbothioamide, m.p. 184°-187° C.;

(±)-anti-N-methyl-2-(3-t.butylamino-2-hydroxypropoxyimino)-1-(3-quinolinyl)cyclohexanecarbothioamide hemihydrate, m.p. 65° C.;

±)-anti-N-methyl-2-isopropoxyimino-1-(3-quinolinyl)-cyclohexanecarbothioamide, m.p. 208°-210° C.;

(±)-anti-N-methyl-2-(4-hydroxybenzyloxyimino) -1-(3-quinolinyl)cyclohexanecarbothioamide hydrate, m.p. 190°-191° C.;

(±)-anti-N-methyl-2-(4-fluorobenzyloxyimino) -1-(3-quinolinyl)cyclohexanecarbothioamide, m.p. 143°-144° C.

EXAMPLE 24

Compounds AL to AY

By proceeding in a similar manner to that hereinbefore described in Example 7, there were prepared:

(±)-anti-N-methyl-2-(4-fluorobenzyloxyimino) -1-(3-pyridyl)cyclohexanecarbothioamide, a white powder; m.p. 110°-11° C.

(±)-anti-N-methyl-2-(2,3,4,5,6-pentafluorobenzyloxyimino) -1-(3-pyridyl)cyclohexanecarbothioamide, m.p. 113°-115° C.;

(±)-anti-N-methyl-2-isopropoxyimino-1-(3-pyridyl)cyclohexanecarbothioamide, m.p. 168°-170° C.;

(±)-anti-N-methyl-2-t.butoxyimino-1-(3-pyridyl)cyclohexanecarbothioamide m.p. 128°-130° C.;

(±)-anti-N-2-[4-(3-t.butylamino-2-hydroxypropoxy)-benzyloxyimino]-1-(3-pyridyl)cyclohexanecarbothioamide, m.p. 39°-43° C.;

(±)-anti-N-methyl-2-(4-hydroxybenzyloxyimino) -1-(3-pyridyl)cyclohexanecarbothioamide, m.p. 169°-171° C.;

(±)-anti-N-methyl-2-(3-fluorobenzyloxyimino) -1-(3-pyridyl)cyclohexanecarbothioamide, m.p. 117°-120° C.;

(±)-anti-N-methyl-2-(2-fluorobenzyloxyimino) -1-(3-pyridyl)cyclohexanecarbothioamide, m.p. 118°-121° C.;

(±)-anti-N-methyl-2-(3-pyridylmethoxyimino) -1-(3-pyridyl)cyclohexanecarbothioamide, m.p. 150°-152° C.;

(±)-anti-N-methyl-2-(4-nitrobenzyloxyimino) -1-(3-pyridyl)cyclohexanecarbothioamide, m.p. 121°-125° C.;

(±)-anti-N-methyl-2-(4-cyanobenzyloxyimino) -1-(3-pyridyl)cyclohexanecarbothioamide, m.p. 125°-136° C.;

(±)-anti-N-methyl-2-(3,4-difluorobenzyloxyimino) -1-(3-pyridyl)cyclohexanecarbothioamide, m.p. 123°-125° C.;

(±)-anti-N-methyl-2-(4-methoxybenzyloxyimino) -1-(3-pyridyl)cyclohexanecarbothioamide, m.p. 101°-103° C.;

(±)-anti-N-methyl-2-(2-trifluoromethylbenzyloxyimino) -1-[3-pyridyl)cyclohexanecarbothioamide hemihydrate, m.p. 133°-136° C.

EXAMPLE 25

By proceeding in a similar manner to Example 15, there was prepared:
the (R)-isomer, by inference, of anti-N-methyl-2-benzyloxyimino-1-(3-pyridyl)cyclohexanecarbothioamide, m.p. 115° C., from N-methyl-2-oxo-1-(3-pyridyl)cyclohexanecarbothioamide (prepared in Example 29); the (R)-isomer, by inference, of anti-N-methyl-2-(4-fluorobenzyloxyimino)-1-(3-pyridyl)cyclohexanecarbothioamide, m.p. 89° C., from N-methyl-2-oxo-1-(3-pyridyl)cyclohexanecarbothioamide (prepared in Example 29); the (S)-isomer, by inference, of anti-N-methyl-2-(4-fluorobenzyloxyimino)-1-(3-pyridyl)-cyclohexanecarbothioamide, m.p. 104°-106° C. from N-methyl-2-oxo-1-(3-pyridyl)cyclohexanecarbothioamide (prepared in Example 14).

EXAMPLE 26

Compound AZ

By proceeding in a similar manner to Example 1 but replacing (±)-2-(3-pyridyl)cyclohexanone by (±)-2-(4-isoquinolinyl)cyclohexanone there was prepared:
(±)-N-methyl-2-oxo-1-(4-isoquinolinyl)cyclohexanecarbothioamide, m.p. 216°-218° C.

(±)-2-(4-Isoquinolinyl)cyclohexanone may be prepared in a similar manner to that hereinbefore described in Reference Example 4.

EXAMPLE 27

Compound BA

By proceeding in a similar manner to Example 7 there was prepared:
(±)-anti-N-methyl-2-benzyloxyimino-1-(4-isoquinolinyl)cyclohexanecarbothioamide 0.75 hydrate, m.p. 166°-168° C.

EXAMPLE 28

Compound BB

By proceeding in a similar manner to Example 1 but replacing (±)-2-(3-pyridyl)cyclohexanone by (±)-2-(5-pyrimidyl)cyclohexanone there was prepared: (±)-N-methyl-2-oxo-1-(5-pyrimidyl)cyclohexanecarbothioamide, m.p. 145°-148° C.

(±)-2-(5-Pyrimidyl)cyclohexanone may be prepared in a similar manner to that hereinbefore described in Reference Example 4.

EXAMPLE 29

By proceeding in a similar manner to Example 14, there was prepared:
the (R)-isomer, by inference, of N-methyl-2-oxo-1-(3-pyridyl)cyclohexanecarbothioamide, m.p. 185° C.

EXAMPLE 30

Compound BC

By proceeding in a similar manner to Example 1 but replacing (±)-2-(3-pyridyl)cyclohexanone by (±)-2-(3-pyridyl)cyclopentanone there was prepared:
(±)-N-methyl-2-oxo-1-(3-pyridyl)cyclopentanecarbothioamide, m.p. 131°-132° C.

(±)-2-(3-Pyridyl)cyclopentanone may be prepared in a similar manner to that hereinbefore described in Reference Example 4.

EXAMPLE 31

Compounds BD, BE and BF

By proceeding in a similar manner to that hereinbefore described in Example 7, there were prepared:
(±)-anti-N-methyl-2-(4-fluorobenzyloxyimino)-1-(3-pyridyl)cyclopentanecarbothioamide, m.p. 105°-106° C.;

(±)-anti-N-methyl-2-methoxyimino-1-(3-pyridyl)cyclopentanecarbothioamide, m.p. 123°-124° C.;

(±)-anti-N-methyl-2-benzyloxyimino-1-(3-pyridyl)cyclopentanecarbothioamide, m.p. 121°-122° C.

EXAMPLE 32

Compound V

To a solution of (±)-anti-2-dimethylhydrazono-1-(3-quinolinyl)cyclohexane (1.34 g, 5 mmol) in dry tetrahydrofuran (10 ml) at −78° C. under an atmosphere of argon was added a solution of 2.5M n-butyl lithium in hexane (4.0 ml, 10 mmol). After stirring at the same temperature for 30 minutes the reaction mixture was treated with a solution of methyl isothiocyanate (0.73 g, 10 mmol) in dry tetrahydrofuran (5 ml) and stirred for a further 30 minutes at −78° C. Finally the mixture was stirred for 2 hours as the temperature was allowed to rise to 25° C. and for 18 hours thereafter. The resultant pale brown solution was treated with a 1% v/v aqueous solution of acetic acid, the crude product extracted using dichloromethane (3×50 ml) and the combined extracts washed with saturated brine solution (40 ml). These extracts were dried over magnesium sulphate and the solvent removed in vacuo to give a red oil, which was purified by flash chromatography over silica gel, using ethyl acetate as eluting solvent, followed by recrystallization from petroleum ether (b.p. 60°-80° C.) to afford (±)-N-anti-methyl-2-dimethylhydrazono-1-(3-quinolinyl)cyclohexanecarbothioamide (0.55 g., 1.6 mmol) as a white solid, melting point 140°-142° C. NMR (CDCl$_3$); 1.62-1.88(c,4H) 1.88-2.08 (c, 1H), 2.40-2.60(s,s,6H), 2.62-2.80 (m,2H), 2.92-3.10 (c,1H), 3.10-3.22 (d,3H), 7.48-7.58 (m,1H), 7.62-7.80 (m,2H), 7.98-8.08 (m,2H), 8.82-8.90 (d,1H), 10.44-10.60 (broad singlet, 1H).

Microanalysis: found; C,66.9; H,7.2; N,16.3; S,9.5%.
C$_{19}$H$_{24}$N$_4$S requires; C,67.0; H,7.1; N,16.5; S,9.4%.

(±)-anti-2-Dimethylhydrazono-1-(3-quinolinyl)cyclohexane was prepared as follows:

To a warm solution of (±)-2-(3-quinolyl)cyclohexanone (9.00 g, 40 mmol) in ethanol (30 ml.) was added 1,1-dimethylhydrazine (3.61 g, 60 mmol) followed by concentrated hydrochloric acid (4 drops). The solution was allowed to stand at 25° C. for 3 days, added to ice (150 g.) and the pH of the mixture adjusted to 9 by the addition of a M aqueous sodium carbonate solution. The crude product was extracted using diethyl ether (3×75 ml), the combined extracts washed with saturated brine solution (50 ml) and dried over magnesium sulphate. Removal of the solvent in vacuo yielded a yellow oil (11.00 g), which was extracted several times with hot portions (40 ml) of n-pentane, the extracts being separated by decantation from insoluble material. The combined, concentrated extracts were kept at 0° C. for several hours to give a solid (10.24 g), which was further purified by recrystallization from n-pentane (40 ml) to afford (±)-anti-2-dimethylhydrazono-1-(3-quinolyl)cyclohexane (7.90 g, 29.5 mmol) as a pale cream solid, melting point 64°-66° C.

NMR (CDCl$_3$); 1.66-1.96 (c,4H), 2.08-2.26 (c,1H), 2.26-2.40 (c,1H), 2.44-2.50 (s,6H), 2.59-2.71 (c,2H), 3.78-3.88 (t,1H), 7.50-7.62 (m,1H), 7.64-7.77 (m,1H), 7.78-7.86 (m,1H), 7.95-8.04 (s,1H), 8.08-8.15 (m,1H), 8.88-8.94 (d,1H).

Microanalysis: found: C,76.3; H,8.0; N,15.6%.
C$_{17}$H$_{21}$N$_3$ requires: C,76.4; H,7.9; N,15.7%.

REFERENCE EXAMPLE 19

A stirred solution of 2-(4-fluorobenzyloxyimino)-1-pyrid-3-ylcyclohexane (150 mg, 0.5 mmol) in tetrahydrofuran (2 ml) at −78° C. was treated with 1.5M butyl lithium in hexane (0.44 ml, 0.65 mmol) over 5 minutes. After 30 minutes at −78° C. the solution was treated with carbon disulphide (57 mg, 0.75 mmol) in tetrahydrofuran (0.5 ml). The temperature of the reaction mixture was then allowed to rise, over 30 minutes to 0° C., and was then treated with a solution of methyl iodide (107 mg, 0.75 mmol) in tetrahydrofuran (0.5 ml) over 10 minutes. The reaction mixture was allowed to warm to 20° C. over 30 minutes, and then concentrated in vacuo. The crude oil was dissolved in dichloromethane (10 ml) and washed successively with water (2×2 ml), and saturated brine (2 ml) then dried over magnesium sulphate. The solution was filtered then concentrated in vacuo to give an amber oil which was purified by flash chromatography over silica gel eluting with ethyl acetate to yield methyl 2-(4-fluorobenzyloxyimino)-1-pyrid-3-ylcyclohexanecarbodithioate (102 mg).

EXAMPLE 33

Compound AL

A stirred solution of methyl 2-(4-fluorobenzyloxyimino)-1-pyrid-3-ylcyclohexanecarbodithioate (20 mg, 0.05 mmol) in ethanol (1 ml) at 20° C. was treated with a 33% w/v solution of methylamine in ethanol (100 µl, 0.8 mmol). After 70 hours at 20° C. the mixture was concentrated in vacuo and the resulting oil recrystallised from cyclohexane to give (±)-anti-N-methyl-2-(4-fluorobenzyloxyimino) -1-(3-pyridyl)cyclohexanecarbothioamide (18 mg).

The NMR characteristics were the same as those of the product described in Example 24.

REFERENCE EXAMPLE 20

A mixture of (±)-2-(3-pyridyl)cyclopentanone (2.0 g) and benzyloxyamine hydrochloride (1.98 g) in anhydrous pyridine was stirred at 60° C. for 4.5 hours. The pyridine was removed in vacuo (40° C., 0.2 mmHg), the residue was dissolved in chloroform (75 ml), washed with water (4×75 ml), dried over magnesium sulphate and evaporated. The residual oil was purified by flash chromatography on silica, eluting with chloroform/methanol (100/1) to give (±)-2-benzyloxyimino -1-(3-pyridyl)cyclopentane (mixture of syn and anti isomers, 1:3), a pale yellow oil (2.91 g).

EXAMPLE 34

Compound BF

A stirred solution of (±)-2-benzyloxyimino -1-(3-pyridyl)cyclopentane (mixture of syn and anti isomers) (2.66 g) in tetrahydrofuran (35 ml), under argon, at −78° C., was treated with 2.5M butyl lithium in hexane (4.6 ml) during 7 minutes at −70° C. After stirring at −70° C. for 35 minutes, the dark red solution was treated with methyl isothiocyanate (0.84 g) in tetrahydrofuran (6 ml). The solution was allowed to warm to 0° C. during 45 minutes and maintained at 0° C. for 1 hour. The solution was partitioned between saturated ammonium chloride solution (40 ml) and ethyl acetate (40 ml). The organic layer was separated and the aqueous layer extracted with ethyl acetate (40 ml). The combined organic layers were washed with water (3×40 ml) dried over magnesium sulphate and evaporated. The residual solid was purified by flash chromatography on silica, eluting with ethyl acetate/toluene (1:2) to give (±)-anti-N-methyl-2-benzyloxyimino-1-(3-pyridyl)cyclopentanecarbothioamide, a colorless solid (1.72 g), m.p. 117°-118.5° C.

The NMR characteristics were the same as those of the product described in Example 31.

EXAMPLE 35

Compound BG

A mixture of the S isomer of N-methyl-2-oxo-1-(3-pyridyl)cyclohexanecarbothioamide (5.56 g; 22.4 mmol) and 2,3,4,5,6-pentafluorobenzyloxyamine hydrochloride (7.0 g; 28 mmol) in pyridine (35 ml) was heated for 24 hours at 60° C. The mixture was poured into water (175 ml) and extracted with ethyl acetate (2×150 ml). The combined organic extracts were then washed with hydrochloric acid (0.002N) until the washings attained pH5. The organic layer was then washed successively with saturated aqueous sodium bicarbonate solution (50 ml), saturated aqueous sodium chloride solution (50 ml) and then dried over magnesium sulphate. Concentration in vacuo afforded a crude oil (8.9 g) which was recrystallized from petrol (60°-80° C.) to give (1S)-anti-N-methyl-2-(2,3,4,5,6-pentafluorobenzyloxyimino)-1-pyrid-3-yl)cyclohexanecarbothioamide (7.4 g), m.p. 114°-116° C Found: C, 54.2; H, 3.9; N, 9.5; S, 7.4%
Calculated for C$_{20}$H$_{18}$F$_5$N$_3$OS: C, 54.2; H, 4.1; N, 9.5; S, 7.2%.
$[\alpha]_D^{25} = -43°(c=1,CHCl_3)$

EXAMPLE 36

Compound BH

A mixture of (−)-N-methyl-2-oxo-1-(3-pyridyl)-cyclohexanecarbothioamide (7.0 g; 28.2 mmol) and 3,4-difluorobenzyloxyamine hydrochloride (8.27 g; 42.4 mmol) in pyridine (100 ml) was heated for 24 hours at 60° C. The mixture was poured into water (500 ml) and the pH adjusted to 9 using saturated aqueous sodium bicarbonate solution. The mixture was then extracted with ethyl acetate (3×150 ml). The combined organic extracts were then washed with hydrochloric acid (0.002N) until the washings attained pH5. The organic layer was then washed successively with saturated aqueous sodium bicarbonate solution (100 ml), water (2×100 ml) and brine (100 ml) and then dried over magnesium sulphate. Concentration in vacuo afforded a crude oil (11.14 g) which was recrystallized from petrol (60°-80° C.) to give (1S)-anti-N-methyl-2-(3,4-difluorobenzyloxyimino)-1-(pyrid-3-yl)cyclohexanecarbothioamide (9.3 g), m.p. 79.5°-81° C.

Found: C, 61.6; H, 5.5; N, 10.7; S, 8.6%

Calculated for $C_{20}H_{21}F_2N_3OS$: C, 61.7; H, 5.4; N, 10.8; S, 8.2%.

$[\alpha]_D^{25} = -67.4°(c=1,CHCl_3)$

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavoring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilizing, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from 0.001 to 50 mg/kg body weight per day by oral administration. By inhalation, either as a nebulized solution or as a formulated dry powder, the preferred daily dosage is from 0.001 to 5 mg/kg body weight. The compounds may also be applied topically for inhibition of head hair loss associated with male pattern baldness, the preferred daily dosage being from 0.1 to 10 mg/kg body weight applied, for example, in 5 ml portions two or three times per day.

The following Examples illustrates pharmaceutical compositions according to the present invention.

COMPOSITION EXAMPLE 1

No. 2 size gelatin capsules each containing:

| | |
|---|---|
| (±)-N-methyl-2-oxo-1-(3-pyridyl)cyclohexanecarbothioamide | 20 mg |
| lactose | 100 mg |
| starch | 60 mg |
| dextrin | 40 mg |
| magnesium stearate | 1 mg | were prepared in accordance with the usual procedure.

COMPOSITION EXAMPLE 2

No. 2 size gelatin capsules each containing:

| | |
|---|---|
| (1S)-anti-N-methyl-2-(2,3,4,5,6-pentafluorobenzyloxyimino-1-(3-pyridyl)cyclohexanecarbothioamide | 20 mg |
| lactose | 100 mg |
| starch | 60 mg |
| dextrin | 40 mg |
| magnesium stearate | 1 mg | were prepared in accordance with the usual procedure.

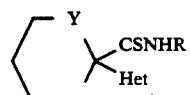

I

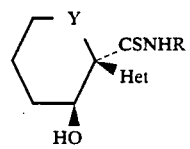

II

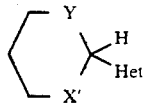

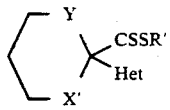

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A thioformamide derivative of the formula:

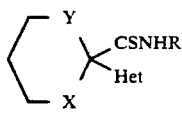

wherein R represents a straight- or branched-chain alkyl radical containing from 1 to 4 carbon atoms, Het represents a tetrahydroquinolin-3-yl, quinolin-3-yl, or pyrid-3-yl radical (optionally substituted by a straight- or branched-chain alkyl or alkoxy radical containing 1 to 4 carbon atoms or by a halogen atom), Y represents an ethylene or methylene radical, or a valency bond, and X represents a carbonyl or hydroxymethylene group or a group of the formula: $>C=NOR^1$, $>C=NN(R^1)_2$ or $>C=NN(R^1)CON(R^1)_2$ in which the symbols $R^1$, which may be the same or different, each represents a hydrogen atom or a straight- or branched-chain alkyl radical containing from 1 to 4 carbon atoms which is unsubstituted or substituted by one or more substituents selected from $C_{2-4}$-alkenyl, carboxy, $C_{2-5}$-alkoxycarbonyl, hydroxy, $C_{1-4}$-alkyl groups), amino, $C_{1-4}$-alkylamino and di-$C_{1-4}$-alkylamino groups or represents a benzyl, phenethyl, 1-naphthylmethyl, 2-naphthylmethyl or pyrid-3-ylmethyl radical each of which may be substituted on the ring by one or more halogen atoms or hydroxy, $C_{1-4}$-alkyl, $C_{1-4}$-alkoxy (alkoxy being unsubstituted or substituted as defined for alkyl groups represented by $R^1$), cyano, nitro, trifluoromethyl, carboxy, $C_{1-4}$-alkylamino, $C_{2-5}$-alkanoylamino, $C_{2-5}$-alkoxycarbonyl groups or two $R^1$ substituents on the same nitrogen atom may together form a straight- or branched-chain alkylene radical containing from 4 to 6 carbon atoms in the chain which is unsubstituted or substituted as defined for alkyl groups represented by $R^1$, or a pharmaceutically acceptable salt thereof.

2. A compound according to claim 1 wherein Y represents a methylene radical or a valency bond.

3. A compound according to claim 1 wherein X represents the carbonyl group or a group of the formula $>C=NOR^1$ wherein $R^1$ is as defined in claim 1.

4. A compound according to claim 1 wherein $R^1$ represents a straight- or branched-chain alkyl radical containing from 1 to 4 carbon atoms which is unsubstituted or substituted as defined in claim 1, or represents a benzyl, phenethyl, 1-naphthylmethyl, 2-naphthylmethyl or pyrid-3-yl-methyl radical each of which may be substituted on the ring as defined in claim 1.

5. A compound according to claim 1 of the formula:

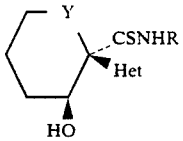

wherein R, Het and Y are as defined in claim 1 in which the hydroxy group is in the trans position relative to the group —CSNHR.

6. A compound according to claim 1 which is selected from the group consisting of:

A (±)-N-methyl-2-oxo-1-(3-pyridyl) cyclohexanecarbothioamide

B (±)-N-methyl-2-oxo-1-(3-quinolinyl) cyclohexanecarbothioamide

C (±)-N-methyl-2-oxo-1-(3-pyridyl) cycloheptanecarbothioamide

D (±)-trans-N-methyl-2-hydroxy-1-(3-pyridyl)cyclohexanecarbothioamide

E (±)-cis-N-methyl-2-hydroxy-1-(3-pyridyl)cyclohexanecarbothioamide

F (±)-anti-N-methyl-2-hydroximino-1-(3-pyridyl)cyclohexanecarbothioamide

G (±)-anti-N-methyl-2-methoxyimino-1-(3-pyridyl)cyclohexanecarbothioamide

H (±)-anti-N-methyl-2-benzyloxyimino-1-(3-pyridyl)cyclohexanecarbothioamide

I (±)-anti-N-methyl-2-hydroxyimino-1-(3-quinolinyl)cyclohexanecarbothioamide

J (2S)-anti-2-(methoxymethyl)-1-[2'-(3-quinolinyl)-2'-methylthiocarbamoylcyclohexylideneamino]-pyrrolidine K (2S)-anti-2-(methoxymethyl)-1-[2'-(3-pyridyl)-2'-methylthiocarbamoylcyclohexylideneamino]-pyrrolidine, L (±)-anti-N-methyl-2-(2-dimethylaminoethoxyimino)-1-(3-pyridyl)cyclohexanecarbothioamide, M (±)-anti-N-methyl-2-(2-aminoethoxyimino)-1-(3-pyridyl)cyclohexanecarbothioamide N (±)-anti-N-methyl-2-methoxycarbonylmethoxyimino-1-(3-pyridyl)cyclohexanecarbothioamide O (±)-anti-N-methyl-2-carbamoylmethoxyimino-1-(3-pyridyl)cyclohexanecarbothioamide, O (±)-anti-N-methyl-2-(2,3-dihydroxypropoxyimino)-1-(3-pyridyl)cyclohexanecarbothioamide Q (±)-anti-N-methyl-2-(2-hydroxyethoxyimino)-1-(3-pyridyl)cyclohexanecarbothioamide R (±)-N-methyl-2-oxo-1-(6-chloropyrid-3-yl)cyclohexanecarbothioamide S (±)-N-methyl-2-oxo-1-(5-bromopyrid-3-yl)cyclohexanecarbothioamide T (±)-N-ethyl-2-oxo-1-(3-pyridyl)cyclohexanecarbothioamide U (±)-N-ethyl-2-oxo-1-(3-quinolinyl)cyclohexanecarbothioamide V (±)-anti-N-methyl-2-dimethylhydrazono-1-(3-quinolinyl)cyclohexanecarbothioamide W (±)-anti-N-methyl-2-diethylhydrazono-1-(3-quinolinyl)cyclohexanecarbothioamide X (±)-anti-N-methyl-2-benzyloxyimino-1-(3-quinolinyl)cyclohexanecarbothioamide Y (±)-anti-N-methyl-2-methoxyimino-1-(3-quinolinyl)-cyclohexanecarbothioamide Z (±)-anti-N-methyl-2-ethoxyimino-1-(3-quinolinyl)cyclohexanecarbothioamide AA (±)-anti-N-methyl-2-butoxyimino-1-(3-quinolinyl)-cyclohexanecarbothioamide AB (±)-anti-N-methyl-2-(3-isopropylamino-2-hydroxypropoxyimino)-1-(3-quinolinyl)cyclohexanecarbothioamide AC (±)-anti-N-methyl-2-t.butoxyimino-1-(3-quinolinyl)cyclohexanecarbothioamide AD (±)-anti-N-methyl-2-prop-2-enoxyimino-1-(3-quinolinyl)cyclohexanecarbothioamide AE (±)-anti-N-methyl-2-naphth-2-ylmethoxyimino-1-(3-quinolinyl)cyclohexanecarbothioamide AF (±)-anti-N-methyl-2-phenethyloximino-1-(3-quinolinyl)cyclohexanecarbothioamide AG (±)-anti-N-methyl-2-naphth-1-ylmethoxyimino-1-(3-quinolinyl)cyclohexanecarbothioamide AH (±)-anti-N-methyl-2-(3-t.butylamino-2-hydroxypropoxyimino-1-(3-quinolinyl)cyclohexanecarbothioamide AI (±)-anti-N-methyl-2-isopropoxyimino-1-(3-quinolinyl)cyclohexanecarbothioamide AJ (±)-anti-N-methyl-2-(4-hydroxybenzyloxyimino-1-(3-quinolinyl)cyclohexanecarbothioamide AK (±)-anti-N-methyl-2-(4-fluorobenzyloxyimino) -1-(3-quinolinyl)cyclohexanecarbothioamide AL (±)-anti-N-methyl-2-(4-fluorobenzyloxyimino) -1-(3-pyridyl)cyclohexanecarbothioamide AM (±)-anti-N-methyl-2-(2,3,4,5,6-pentafluorobenzyloxyimino)-1-(3-pyridyl)cyclohexanecarbothioamide AN (±)-anti-N-methyl-2-isopropoxyimino-1-(3-pyridyl)cyclohexanecarbothioamide AO (±)-anti-N-methyl-2-t.butoxyimino-1-(3-pyridyl)-cyclohexanecarbothioamide AP (±)-anti-N-methyl-2-[4-(3-t.butylamino-2-hydroxypropoxy)benzyloxyimino]-1-(3-pyridyl)cyclohexanecarbothioamide AQ (±)-anti-N-methyl-2-(4-hydroxybenzyloxyimino) -1-(3-pyridyl)cyclohexanecarbothioamide AR (±)-anti-N-methyl-2-(3-fluorobenzyloxyimino) -1-(3-pyridyl)cyclohexanecarbothioamide AS (±)-anti-N-methyl-2-(2-fluorobenzyloxyimino) -1-(3-pyridyl)cyclohexanecarbothioamide AT (±)-anti-N-methyl-2-(3-pyridylmethoxyimino) -1-(3-pyridyl)cyclohexanecarbothioamide AU (±)-anti-N-methyl-2-(4-nitrobenzyloxyimino) -1-(3-pyridyl)cyclohexanecarbothioamide, AV (±)-anti-N-methyl-2-(4-cyanobenzyloxyimino) -1-(3-pyridyl)cyclohexanecarbothioamide AW (±)-anti-N-methyl-2-(3,4-difluorobenzyloxyimino) -1(3-pyridyl)cyclohexanecarbothioamide AX (±)-anti-N-methyl-2-(4-methoxybenzyloxyimino) -1-(3-pyridyl)cyclohexanecarbothioamide AY (±)-anti-N-methyl-2-(2-trifluoromethylbenzyloxyimino) -1-(3-pyridyl)cyclohexanecarbothioamide BC (±)-N-methyl-2-oxo-1-(3-pyridyl)cyclopentanecarbothioamide BD (±)-anti-N-methyl-2-(4-fluorobenzyloxyimino) -1-(3-pyridyl)cyclopentanecarbothioamide BE (±)-anti-N-methyl-2-methoxyimino-1-(3-pyridyl)-cyclopentanecarbothioamide BF (±)-anti-N-methyl-2-benzyloxyimino-1-(3-pyridyl)-cyclopentanecarbothioamide.

BG (1S)-anti-N-methyl-2-(2,3,4,5,6-pentafluorobenzyloxyimino-1-(3-pyridyl)cyclohexanecarbothioamide; and BH (1S)-anti-N-methyl-2-(3,4-difluorobenzyloxyimino-1-(3-pyridyl)cyclohexanecarbothioamide or a pharmaceutically acceptable salt thereof.

7. A pharmaceutical composition which comprises an effective amount of a thioformamide derivative of formula (I) as defined in claim 1 or a pharmaceutically acceptable salt thereof in association with a pharmaceutically acceptable carrier or coating.

8. A method of inhibiting head hair loss associated with male pattern baldness which comprises the topical administration of an amount effective to inhibit said hair loss of a thioformamide derivative of formula (I) as defined in claim 1 or a pharmaceutically acceptable salt thereof.

* * * * *